US 6,667,762 B1

(12) United States Patent
Bouvier et al.

(10) Patent No.: US 6,667,762 B1
(45) Date of Patent: Dec. 23, 2003

(54) MINIATURE INSPECTION SYSTEM

(75) Inventors: William P. Bouvier, New Boston, NH (US); Timothy P. White, New Boston, NH (US); John J. Merva, Weare, NH (US)

(73) Assignee: Robotic Vision Systems, Inc., Canton, MA (US)

( * ) Notice: Subject to any disclaimer, the term of this patent is extended or adjusted under 35 U.S.C. 154(b) by 0 days.

(21) Appl. No.: 09/701,321

(22) PCT Filed: May 28, 1999

(86) PCT No.: PCT/US99/11937

§ 371 (c)(1),
(2), (4) Date: Feb. 16, 2001

(87) PCT Pub. No.: WO99/62263

PCT Pub. Date: Dec. 2, 1999

(51) Int. Cl.[7] .............................. H04N 7/18; H04N 9/47
(52) U.S. Cl. ........................................ 348/92; 348/131
(58) Field of Search ........................... 348/92, 125, 126, 348/131, 133; 382/147, 148, 149, 150; H04N 7/18, 9/47

(56) References Cited

U.S. PATENT DOCUMENTS

| 4,618,938 | A | 10/1986 | Sandland et al. |
| 4,639,587 | A | 1/1987 | Chadwick et al. |
| 5,298,989 | A | 3/1994 | Tsukahara et al. |
| 5,386,293 | A | 1/1995 | Barnard et al. |
| 5,420,689 | A | 5/1995 | Siu |
| 5,455,870 | A | 10/1995 | Sepai et al. |
| 5,623,303 | A | 4/1997 | Inoue et al. |
| 5,867,741 | A | 2/1999 | Maruyama et al. |
| 5,877,494 | A | 3/1999 | Larsen et al. |
| 6,177,954 | B1 * | 1/2001 | Bouvier ...................... 348/92 |

* cited by examiner

*Primary Examiner*—Nhon Diep
(74) *Attorney, Agent, or Firm*—Davis & Bujold, P.L.L.C.

(57) ABSTRACT

A miniature inspection system for observing an object. The system comprises a camera (4) defining an optical axis (8) defined between the camera (4) and the object when located at the object inspection location. A ring light (14) is located concentrically with respect to and along the optical axis at a location between an entrance aperture of the camera (4) and the object, when located at the object observing location. A field lens (10) is located along the optical axis at a location between the camera (4) and the object, when placed at the object observing location. A mirror or a penta-prism (34) may be located along the optical axis, between the camera (4) and the field lens, so that light reflected from the object along the optical axis is reflected by either the mirror or the penta-prism (34) toward the entrance aperture of the camera (4). An illumination source (50), may be also provided to supply illumination along the optical axis of the system.

19 Claims, 12 Drawing Sheets

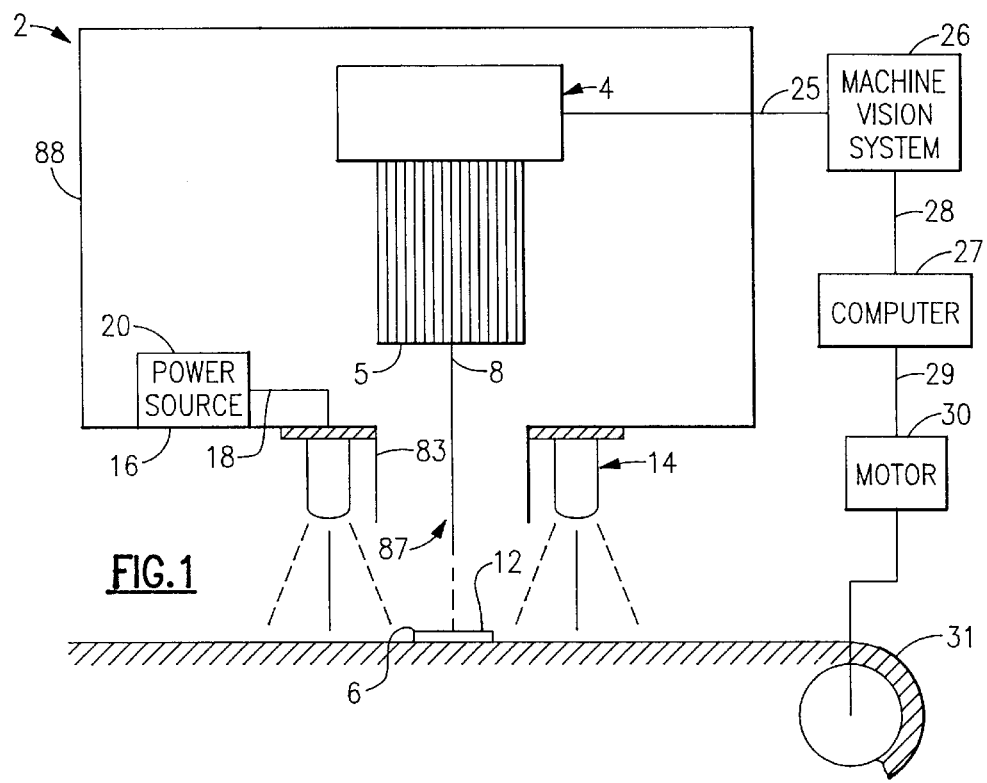
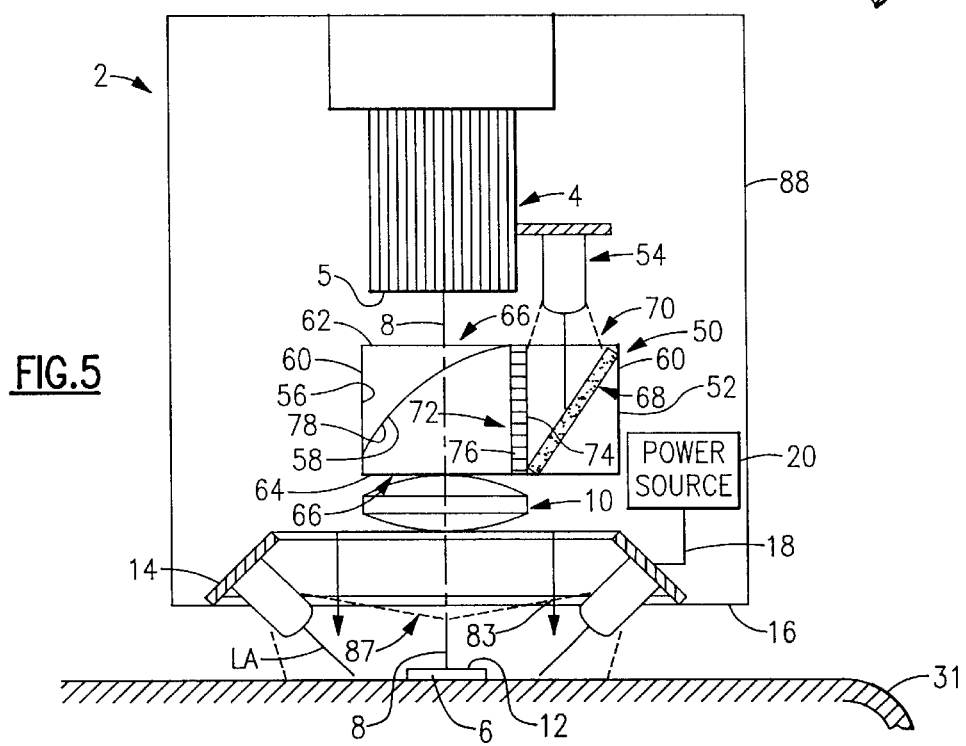

MINIATURE INSPECTION SYSTEM

The present invention relates to a mounted camera used in conjunction with and an illumination source, and possibly a field lens, to provide a compact inspection system which is extremely small in size and facilitates use within the small confines of semiconductor, processing equipment.

BACKGROUND OF THE INVENTION

There are a variety of known illumination sources for illuminating a flat surface to be inspected such as a laser-etched art work semiconductor lead framework. However, most of the known systems are of a relatively large size which do not easily fit within the confines of currently available semiconductor processing equipment.

In particular, known arrangements typically affix a ring of LEDs to the underside of rather large and bulky inspection equipment. The ring of LEDs is centered about the optical axis which extends normal to the inspection surface. This illumination geometry is useful for imaging "mirror melting" by a laser of desired art work on a diffusely reflecting metal surface. In the area affected by the laser, the diffused surface finish is melted to convert that surface area into a highly specular surface finish. This specular surface finish reflects the low-angle dark field illumination off at an equivalent low-angle causing it to appear dark in the field of view. The diffuse background finish reflects some of the incident low-angle illumination along the optical axis into the camera lens and hence that area appears bright. This combination causes the "mirror melting" laser mark to appear in high contrast, e.g. black on a white surface, rendering it fairly easy to decipher by conventional machine vision systems.

If the lead frame surface finish is highly specular, however, the dark field illumination geometry described above will cause the surface to appear black, hence rendering invisible any "mirror melting" art work, e.g. a dark field on a dark field. For laser etching to be visible under a dark field illumination, on such highly specular surface, the surface must be optically "roughed up" by the laser. For example, the surface must be etched so as to form small craters or pits. Under darkfield illumination, only the rim of the laser pits will reflect light to the camera while the valleys of the pits will reflect the light to the surrounding environment. If the pits are small enough and spaced closely enough together they can be made to appear as a "solid" feature. If the pits are isolated and enlarged, however, they appear as bright rings on a dark background, potentially causing problems with the inspection algorithms currently used in prior art systems.

SUMMARY OF THE INVENTION

Wherefore, it is an object of the present invention to overcome the aforementioned problems and drawbacks associated with the prior art designs.

In one embodiment, the present invention relates to a design which provides a bright field illumination via a curved beam splitter which is positioned between the camera lens and a penta-prism. In applications where the mark being imaged is relatively small, the bright field source does not have to be significantly larger in size than the camera aperture itself.

The invention relates to a miniature inspection system for observing an object, the inspection system comprising: a camera for inspecting an object when located at an inspection location, and an optical axis being defined between the camera and the object when located at the object inspection location; a ring light being located concentrically with respect to and along the optical axis, at a location between an entrance aperture of the camera and the object, when located at the object observing location; and a field lens being located along the optical axis at a location between the camera and the object, when placed at the object observing location.

The present invention also relates to a miniature inspection system for observing an object, the inspection system comprising: a camera for inspecting an object when located at an inspection location, and an optical axis being defined between the camera and the object when located at the object inspection location; a ring light being concentrically disposed with respect to and along the optical axis at a location between an entrance aperture of the camera and the object, when located at the object observing location; and a penta-prism being located along the optical axis such that light reflected from the object, along the optical axis, is reflected by the penta-prism along the optical axis toward the entrance aperture of the camera.

Also, the present invention relates to a miniature inspection system for observing an object, the inspection system comprising: a camera for inspecting an object when located at an inspection location, and an optical axis being defined between the camera and the object when located at the object inspection location; a ring light being concentrically disposed with respect to and along the optical axis at a location between an entrance aperture of the camera and the object, when located at the object observing location; and a fresnel lens being located between the ring light and the object, when placed at the object inspection location, for altering the light supplied to the object when placed at the object inspection location.

The term "diffuse", as used in this specification and the appended claims, means a light source which is dispersed over a broad range of incident angle of azimuth and elevation with respect to the object being observed, and the light source approaches complete coverage over the area where the light is directed, i.e. greater than 25% of the possible angular range of incident light. The term "concealed", as used in this specification and appended claims, when referring to the diffuser and the object to be inspected, means that the surface emitting the diffused light from the diffuser is positioned such that the emitting surface of the diffuser can not directly illuminate the object, i.e. only indirect illumination of the object by reflection of light off the beam splitter or the side wall (s) of the housing or supplying light through the beam splitter can occur.

BRIEF DESCRIPTION OF THE DRAWINGS

The invention will now be described, by way of example, with reference to the accompanying drawings in which:

FIG. 1 is a diagrammatic representation of a first embodiment of the inspection system according to the present invention;

FIG. 5 is a diagrammatic representation of a fifth embodiment of the inspection system according to the present invention;

DESCRIPTION OF THE PREFERRED EMBODIMENT(S)

Figure 2:
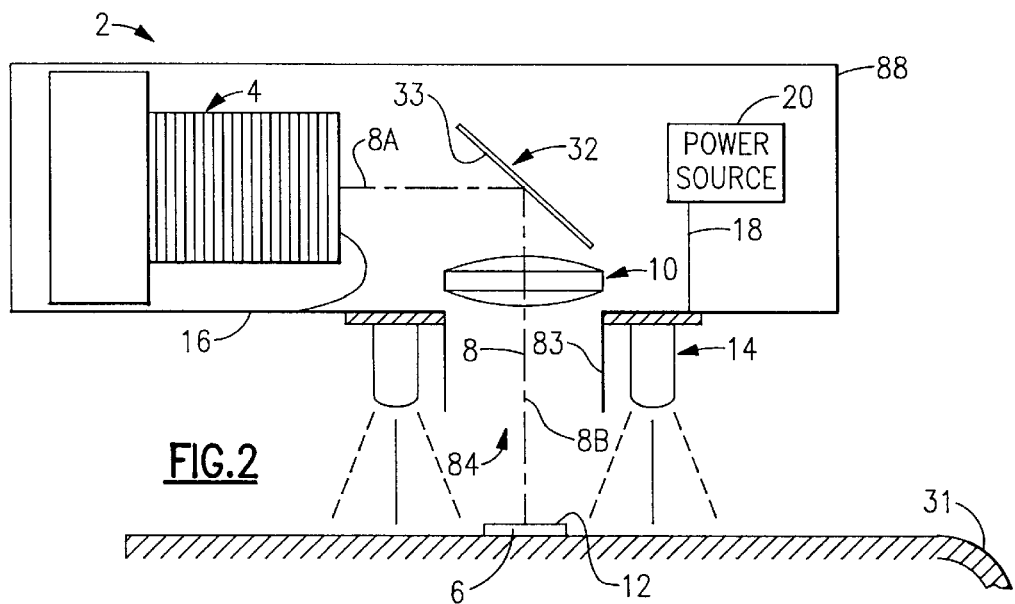
FIG. 2 is a diagrammatic representation of a second embodiment of the inspection system according to the present invention.

With reference to FIG. 1, a first embodiment of the present invention will now be described in detail. As can be seen is FIG. 1, the inspection system generally comprises a board-level miniature video camera 4, such as a CCD (charge coupled device) camera, a CMOS (metal oxide semiconductor) camera or some other observation or inspection device which is well known in the art. The camera 4 is positioned for viewing an object 6 to be inspected and an optical axis 8 is defined between the camera 4 and the object 6.

A ring of LEDs 14 is affixed to the underside of the system 2, e.g. to conventional framework 16 of the system, and the optical axis 8 extends through the center of the ring of LEDs 14. The ring of LEDs 14 is powered, via electrical wiring 18, by an appropriate power source 20 to facilitate illumination of the top surface of the object 6 to be inspected by the ring of LEDs 14. During use, the light from the LEDs 14 is supplied toward the object 6 to be inspected. Some of the light supplied by the ring of LEDs 14 is reflected by the surface 12 of the object 6 to be inspected to the surrounding environment. The remaining light, supplied by the ring of LEDs 14, is reflected off the surface 12 of the object 6 along the optical axis 8 toward the camera lens aperture 5. The light finally enters the camera 4, via the lens entrance aperture 5, and is appropriately sensed by the internal sensing mechanism of the camera 4. As such feature is well known to those skilled in this art, a further detailed description concerning the same is not provided herein.

The camera 4 is, in turn, coupled to a machine vision system 26 (only diagrammatically shown), via a conventional cable 25, for determining the sensed image, e.g. by a comparison of the sensed image with prior input features, images, characters, objects, contours, shapes, indicia, etc. Once the desired characteristic, feature, etc., of the object(s) 6 to be observed or inspected is determined by the system 2, the object(s) 6 can then be further manipulated by the system, e.g. the object can be accepted or rejected, can be package or further conveyed, can be sorted by size, shape, or type, etc., depending upon the particular application. The machine vision system 26, in turn, is connected to a computer 27 via a conventional cable 28. The computer 27 is typically electrically connected, by a cable 29, to a motor 30 which drives a conveyor 31 or some other transportation or conveying device for controlling further manipulation or manufacturing of the object 6, e.g. for inspection, transportation, processing, sorting, orientation, etc. As the present invention primarily relates to the inspection system 2, a further detailed description concerning the machine vision system 26 and its associated components will not be provided.

Turning now to FIG. 2, a second embodiment of the present invention will now be described. As this embodiment is very similar to the first embodiment, only the variations between this embodiment and the first embodiment will be described in detail. The primary difference between the second embodiment and the first embodiment is that the camera 4 is positioned such that a first portion 8A of the optical axis 8 extends substantially parallel, to the top surface 12 of the object 6 to be inspected. Secondly, a right angle mirror 32 is located along the optical axis 8 to alter the path of the optical axis 8B so that it extends substantially perpendicular to the top surface 12 of the object 6. As can be seen in FIG. 2, the right angle mirror 32 has a reflective surface 33 for reflecting light from the object 6 toward the camera 4. The reflective surface 33 is disposed at an angle of approximately 45° with respect to the optical axis 8 of the camera 4.

Lastly, a field lens 10 is positioned along the optical axis 8, at a location between a camera lens entrance aperture 5 and an inspection surface 12 of the object 6. It is to be appreciated that the field lens 10 is supported by the system 2 in a conventional manner (not shown in detail) such that the field lens 10 can be readily interchanged or replaced with a variety of other field lens, having different focusing characteristics, so that by selecting an appropriate power of the field lens a wide range of optical magnifications and/or fields of view can be achieved by the system 2. The interchangeable or replaceable field lens feature provides additional flexibility to the basic design of the present invention.

When light is supplied by the LEDs 14 toward the surface 12 of the object 6 to be inspected, some of the light supplied by the ring of LEDs 14 is reflected by the surface 12 of the object 6 to be inspected to the surrounding environment. The remaining light, supplied by the ring of LEDs 14, is reflected off the surface 12 of the object 6 along the optical axis 8 toward the field lens 10. The reflected light, passing through the field lens 10, is focused and then is supplied to and reflected off the reflective surface 33 of the right angle mirror 32 toward the lens entrance aperture 5 of the camera 4. The focused light finally enters the camera 4 and is appropriately sensed by the internal sensing characteristics of the camera 4.

Figure 3:
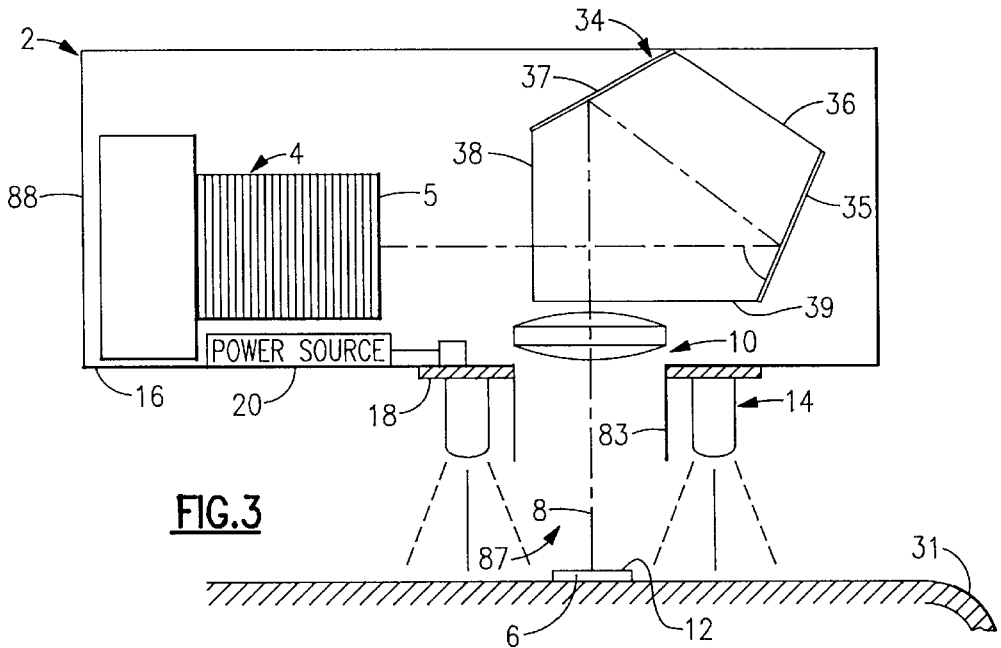
FIG. 3 is a diagrammatic representation of a third embodiment of the inspection system according to the present invention.

Turning now to FIG. 3, a third embodiment of the present invention will now be described. As this embodiment is very similar to the second embodiment, only the variations between this embodiment and the second embodiment will be described in detail. The primary difference between the third embodiment and the second embodiment is that a penta-prism 34, rather than a right angle mirror 32, is located along the optical axis 8 to alter the path of the optical axis B. As can be seen in FIG. 3, the penta-prism 34 has five surfaces 35, 36, 37, 38 and 39. Only two of these surfaces are utilized for reflecting light, e.g. the first and second reflective surfaces 35 and 37, respectively, while two other surfaces are utilized for transmitting light, e.g. the first and second transmissive surfaces 38 and 39, respectively. The first reflective surface 35 is disposed at approximately 67.5° with respect to the optical axis 8 of the camera 4 while the second. reflective surface 37 is disclosed at approximately 22.5° with respect to the optical axis 8 of the camera 4. The first and second transmissive surfaces 38 and 39 both lie substantially normal, e.g. lie at an angle of about 90°, respectively, with respect to the optical axis 8.

When light is supplied by the LEDs 14 toward the surface 12 of the object 6 to be inspected, some of the light supplied by the ring of LEDs 14 is reflected by the surface 12 of the object 6 to be inspected to the surrounding environment. The remaining light, supplied by the ring of LEDs 14, is reflected off the surface 12 of the object 6 along the optical-axis 8.toward the field lens 10. The reflected light, passing through the field lens 10, is focused and then supplied to and enters the second transmissive surface 39 of the penta-prism 34, which is arranged substantially normal to the optical axis 8, so the light passes substantially directly therethrough and is substantially unaltered by the second transmissive surface 39. The light then is reflected off the second reflective surface 37 of penta-prism 34 toward the first reflective surface 35 of the penta-prism 34. The light then reflects off the first reflective surface 35 of the penta-prism and exits through the first transmissive surface 38 of the penta-prism and is supplied toward the lens entrance aperture 5 of the camera 4. The focused light finally enters the camera 4 and is appropriately sensed by the internal sensing characteristics of the camera 4.

Figure 4:
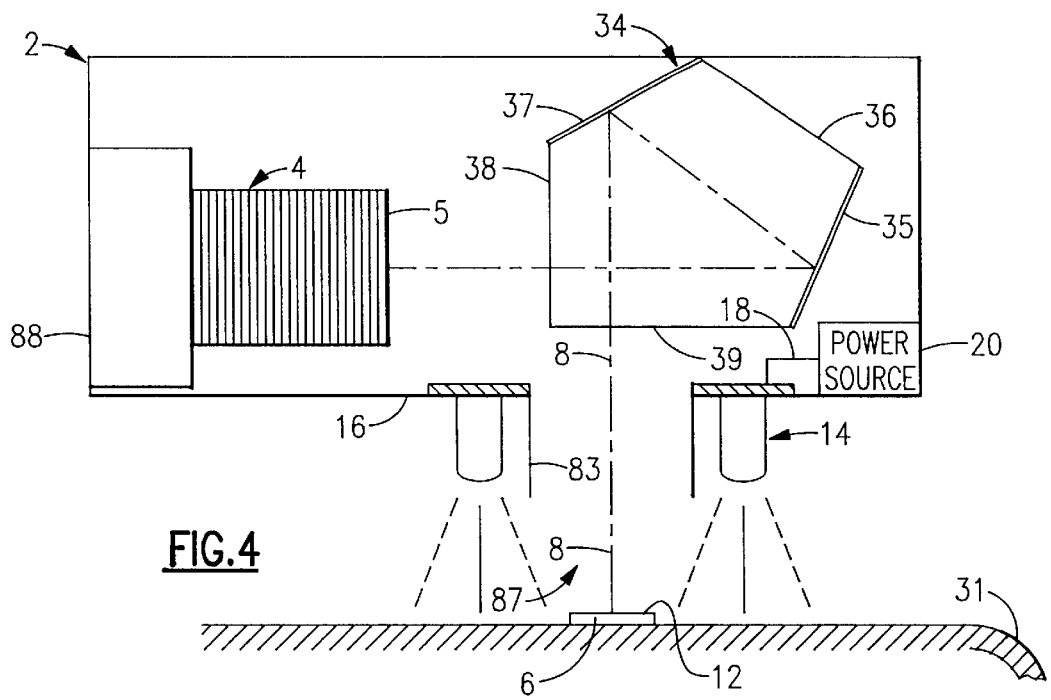
FIG. 4 is a diagrammatic representation of a fourth embodiment of the inspection system according to the present invention.

Turning now to FIG. 4, a fourth embodiment of the present invention will now be described. As this embodiment is very similar to the third embodiment, only the variations between this embodiment and the third embodiment will be described in detail. The primary difference between the fourth embodiment and the third embodiment is the elimination of the field lens 10 in the fourth embodiment.

As can be seen in FIG. 4, when light is supplied by the LEDs 14 toward the surface 12 of the object 6 to be inspected, some of the light supplied by the ring of LEDs 14 is reflected by the surface 12 of the object 6 to be inspected to the surrounding environment. The remaining light, supplied by the ring of LEDs 14, is reflected off the surface 12 of the object 6 along the optical axis 8, toward the penta-prism 34. The reflected light enters the second transmissive surface 39 of the penta-prism 34, which is arranged substantially normal to the optical axis 8, so the light passes substantially directly therethrough. The light then is reflected off the second reflective surface 37 of penta-prism 34 toward the first reflective surface 35 of the penta-prism. The light then reflects off the first reflective surface 35 of the penta-prism and exits through the first transmissive surface 38 of the penta-prism toward the lens entrance aperture 5 of the camera 4. The focused light finally enters the camera 4 and is appropriately sensed by the internal sensing characteristics of the camera 4.

With reference to FIG. 5, a fifth embodiment of the present invention will now be described in detail. As this embodiment is very similar to the first embodiment, only the variations between this embodiment and the first embodiment will be described in detail. The primary difference between the fifth embodiment and the first embodiment is the addition of a field lens 10 and a diffuse illumination source 50, for providing light along the optical axis 8. The field lens 10 is positioned along the optical axis 8, at a location between the camera lens entrance aperture 5 and the inspection surface 12 of the object 6. The diffuse illumination source 50 is positioned along the optical axis, at a location between the camera lens entrance aperture 5 and the field lens 10, to provide illumination along the optical axis 8. The illumination source 50, for providing light along the optical axis 8, has a rectangular housing 52, a light source 54, a light trap 56 and a beam splitter 58, e.g. which can be a curved beam splitter rather than a flat planar beam splitter. The beam splitter 58 reflects a desired amount of supplied light, e.g. between about 20% to 80% and preferably about 50%, along the optical axis 8 toward the object 6 while also allowing a desired amount of light, e.g. about 20% to 80% and preferably about 50%, of the light reflected by the surface 12 of the object 6 to be inspected to pass through the beam splitter 58 and be viewed by the camera 4.

The housing 52 comprises a first pair of spaced apart parallel end walls 60, a pair of spaced apart parallel side walls (not shown) and a roof wall 62 and a base wall 64. An aperture 6 is formed in both the roof wall 62 and the base wall 64 and the apertures 66 are concentric with respect to one another and located along the optical axis 8. The housing 52 supports the light source 54 which is located adjacent the roof wall 62 and positioned to supply light to a diffuser 68, accommodated within the housing 52, through a further opening 70 provided in the housing 52. The beam splitter 58 is located remote from the light source 54 and positioned obliquely relative to and along the optical axis 8. The light diffuser 68 is located between the light source 54 and the beam splitter 58, and the light trap 56 is supported by an inner surface of the end wall 60 located adjacent the beam splitter 58. In addition, a microlouver filter 72 is positioned between the diffuser 68 and the beam splitter 58. The microlouver filter 72 is located immediately adjacent the diffuser 68 and extends parallel to a plane defined by the optical axis 8. The microlouver filter 72 generally has a thickness of from about 0.010 to about 0.060 inch, for example. The microlouver filter 72 is fastened or otherwise secured to an inner surface of the housing 52 in a conventional manner.

The microlouver filter 72 comprises a generally high performance plastic film 74 containing a plurality of closely spaced and parallelly arranged microlouvers (not shown in specific detail) therein. These microlouvers simulate the characteristics of tiny venetian blinds which block out unwanted ambient light and facilitate control of the illumination direction of the diffused light which is supplied from the diffuser 68 to the beam splitter 58, e.g. the microlouvers of the microlouver filter 72 facilitate the supply of light in a more parallel fashion and prevent light supplied by the diffuser 68 from indirectly illuminating the object 6 to be inspected.

The microlouvers lie in a plane which forms an angle of about 45° to 90°, preferably about 90°, with respect to a light transmission surface 76 of the microlouver filter 72, i.e. they extend perpendicular to the light transmission surface 76. It is to be appreciated that the thickness of the microlouver filter 72 must be sufficient so that the tiny venetian blinds or microlouvers prevent any of the diffused light, diffused by the diffuser 68, from directly illuminating the object 6 to be inspected. Accordingly, the spacing of the microlouvers from one another, the angle of microlouvers relative to the light receiving surface 74 and the light transmission surface 76 and the thickness of the microlouver filter 72 have to be taken into consideration, when selecting an appropriate microlouver filter 72, to prevent direct illumination by the diffuser 68 of the object 6 to be inspected.

One suitable microlouver filter 72 is a light control film product manufactured by Minnesota Mining and Manufacturing Company of St. Paul, Minn. and sold by their 3M Safety and Security Systems Division under the "3M Light Control Film" brand name. The microlouver filter 72 can be made from polycarbonate or cellulose acetate butyrate and generally has a thickness of about 0.030 inches, or so.

The arrangement of these components is such that the light source 54 casts light upon the diffuser 68 which, in turns, diffuses the light from the light source 54 and casts the diffused light upon the light receiving surface of the microlouver filter 72 which, in turns, casts the diffused light from the light source 54 upon the beam splitter 58. The beam splitter 58 has a partially reflective first surface 78. A desired portion of the light, e.g. approximately one half of the light from the microlouver filter 72 impacting upon the reflective first surface 78 of the beam splitter 58 is reflected toward the object 6, while the remainder of the light, e.g. approximately one half of the light from the microlouver filter 72, passes through the beam splitter 58 and is absorbed by the light trap 56. Likewise, a portion of the light reflected back by the object 6, along the optical axis 8, is transmitted through the beam splitter 58, along the optical axis 8, toward the lens entrance aperture 5 of the camera 4 for viewing while a remainder of the light is reflected back toward the microlouver filter 72.

A second difference, between the fifth embodiment and the first embodiment, is that the ring of LEDs 14, affixed to the underside of the system 2 via the conventional framework 16, is arranged at an angle with respect to the optical axis 8, e.g. the LEDs each define a longitudinal axis LA which lies at an angle of about 45° or so with respect to the optical axis 8. The ring of LEDs 14, however, is still centered with respect to the optical axis 8. The ring of LEDs, in this embodiment, comprises a circuit which is bent into a conical or domed configuration with all of the installed LEDs (lighting elements) facing inwardly toward the object 6. All the LEDs are preferably supplied with electrical power via a common bus having one power source 20 or a plurality of power sources for supplying power to the LEDs, as with the prior embodiments of the present invention. This domed configuration of the LEDs facilitates more direct illumination of the object 6 to be inspected by the LEDs.

During use, the light from the LEDs 14 is supplied toward the object 6 to be inspected. In addition, light is also supplied along the optical axis 8 via the illumination source 50, for providing light along the optical axis 8. Some of the light supplied by the two light sources 14, 50 is reflected by the surface 12 of the object 6 to be inspected to the surrounding environment. The remaining light, supplied by the two light sources 14, 50, is reflected off the surface 12 of the object 6 along the optical axis 8 toward the field lens 10. The reflected light enters a first surface 22 of the field lens 10 and is altered by the internal focusing characteristics of the field lens 10. The focused light then exits the rear surface 24 of the field lens 10 and is supplied toward the curved beam splitter 58. The beam splitter reflects a desired amount of light, e.g. between about 20% to 80% and preferably about 50%, back toward the microlouver 72 while allowing a desired amount of reflected light, e.g. about 20% to 80% and preferably about 50%, reflected by the object 6 to be inspected to pass therethrough and enter the lens entrance aperture 5 of the camera 4. The focused light finally enters the camera 4 and is appropriately sensed by the internal sensing characteristics of the camera 4.

Figure 6:
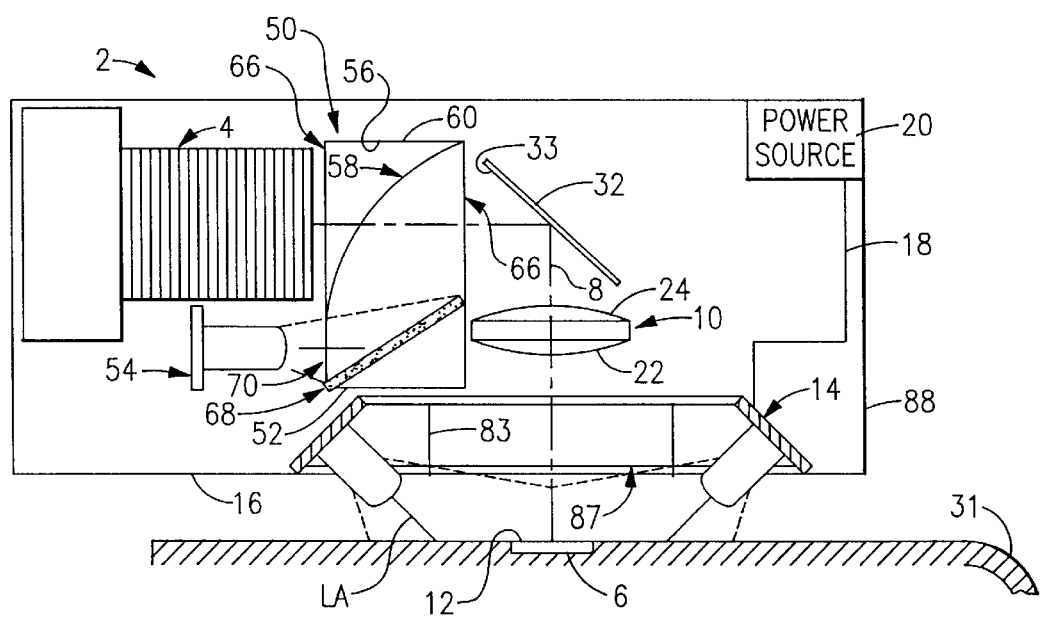
FIG. 6 is a diagrammatic representation of a sixth embodiment of the inspection system according to the present invention.

Turning now to FIG. 6, a sixth embodiment of the present invention will now be described. As this embodiment is very similar to the second embodiment, only the variations between this embodiment and the second embodiment will be described in detail. The primary difference between the sixth embodiment and the second embodiment is that an illumination source 50, for providing light along the optical axis 8, is positioned along the optical axis 8 at a location between the lens entrance aperture 5 of the camera 4 and the right angle mirror 32 to provide illumination along the optical axis 8. In addition, the illumination source 50 does not contain a microlouver, between the reflective diffuser 68 and the curved beam splitter 58 (it is not required in this embodiment). A third difference is that each LED of the ring of LEDs 14 is arranged at an angle with respect to the optical axis 8, e.g. the LEDs each define a longitudinal axis LA which lies at an angle of about 45° or so with respect to the optical axis 8 (the LEDs are very similar to the arrangement described with respect to FIG. 5).

During use, the light from the LEDs 14 is supplied toward the object 6 to be inspected. In addition, light is also supplied along the optical axis 8 via the illumination source 50. The light supplied from the illumination source 50 is directed by the beam splitter 58 toward the right angle mirror 32 which, in turn, reflects the supplied light at the field lens 10 for supplying illumination along the optical axis 8. The field lens 10, in turn, focuses the light at the surface 12 of the object 6 to be inspected. Some of the light supplied by the two light sources 14, 50 is reflected by the surface 12 of the object 6 to be inspected to the surrounding environment. The remaining light, supplied by the two light sources 14, 50, is reflected off the surface 12 of the object 6 along the optical axis 8 toward the field lens 10. The light enters a first surface 22 of the field lens 10 and is altered by the internal focusing characteristics of the field lens 10. The focused light then exits the rear surface 24 of the field lens 10 and is supplied toward the right angle mirror 32. The reflected light then reflects off the reflective surface 33 of the right angle mirror 32 toward the curved beam splitter 58. The beam splitter 58 reflects a desired amount of light, e.g. between about 20% to 80% and preferably about 50%, back toward the diffuser 68 while allowing a desired amount of reflected light, e.g. about 20% to 80% and preferably about 50%, reflected by the object 6 to be inspected to pass therethrough and enter the lens entrance aperture 5 of the camera 4. The focused light finally enters the camera 4 and is appropriately sensed by the internal sensing characteristics of the camera 4.

Figure 7:
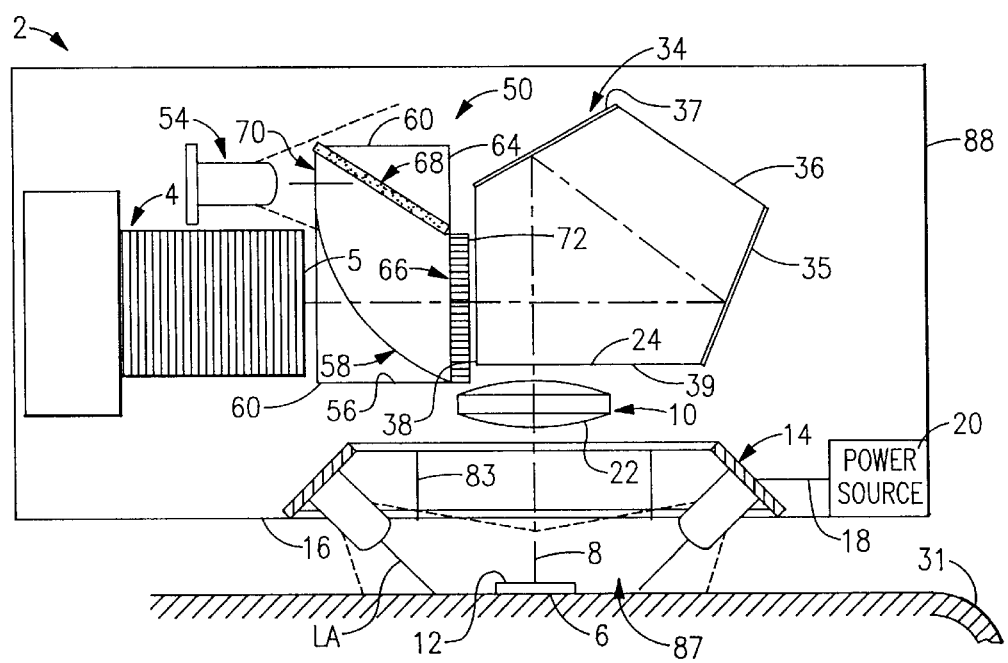
FIG. 7 is a diagrammatic representation of a seventh embodiment of the inspection system according to the present invention.

Turning now to FIG. 7, a seventh embodiment of the present invention will now be described. As this embodiment is very similar to the third embodiment, only the variations between the seventh embodiment and the third embodiment will be described in detail. The primary difference between the seventh embodiment and the third embodiment is that an illumination source 50, for providing light along the optical axis 8, is positioned along the optical axis 8 at a location between the camera lens entrance aperture 5 and the penta-prism 34 to provide illumination along the optical axis 8. In addition, the illumination source 50 has a microlouver 72 located to completely cover the aperture 66 provided in the base wall 64 of the illumination source 50. A third difference is that each LED of the ring of LEDs 14 is arranged at an angle with respect to the optical axis 8, e.g. the LEDs each define a longitudinal axis which lies at an angle of about 45° or so with respect to the optical axis 8 (substantially the same as the LED arrangement of FIGS. 5 and 6).

During use, the light from the LEDs 14 is supplied toward the object 6 to be inspected. In addition, light is also supplied along the optical axis 8 via the illumination source 50. The light supplied from the illumination source 50 is directed at the penta-prism 34 which, in turn, reflects the supplied light off the first and the second reflective surfaces 35, 37 toward the field lens 10 for focussing and supplying illumination along the optical axis 8. Some of the light supplied by the two light sources 14, 50 is reflected by the surface 12 of the object 6 to be inspected to the surrounding environment. The remaining light, supplied by the two light sources 14, 50, is reflected off the surface 12 of the object 6 along the optical axis 8 toward the field lens 10. The light enters a first surface 22 of the field lens 10 and is altered by the internal focusing characteristics of the field lens 10. The focused light then exits the rear surface 24 of the field lens 10 and is supplied toward the second transmissive surface 39 of the penta-prism 34, which is arranged substantially normal to the optical axis 8, so that the light passes substantially directly therethrough. The light then is reflected off the second reflective surface 37 of penta-prism 34 toward the first reflective surface 35 of the penta-prism. The light then reflects off the first reflective surface 35 of the penta-prism and exits through the first transmissive surface 38 of the penta-prism toward the microlouver 72. The light passes through the microlouver 72 and then contacts the curved beam splitter 58. The beam splitter 58 reflects a desired amount of light, e.g. between about 20% to 80% and preferably about 50%, back toward the diffuser 68 while allowing a desired amount of reflected light, e.g. about 20% to 80% and preferably about 50%, reflected by the object 6 to be inspected to pass therethrough and enter the lens entrance aperture 5 of the camera 4. The focused light finally enters the camera 4 and is appropriately sensed by the internal sensing characteristics of the camera 4.

Figure 8:
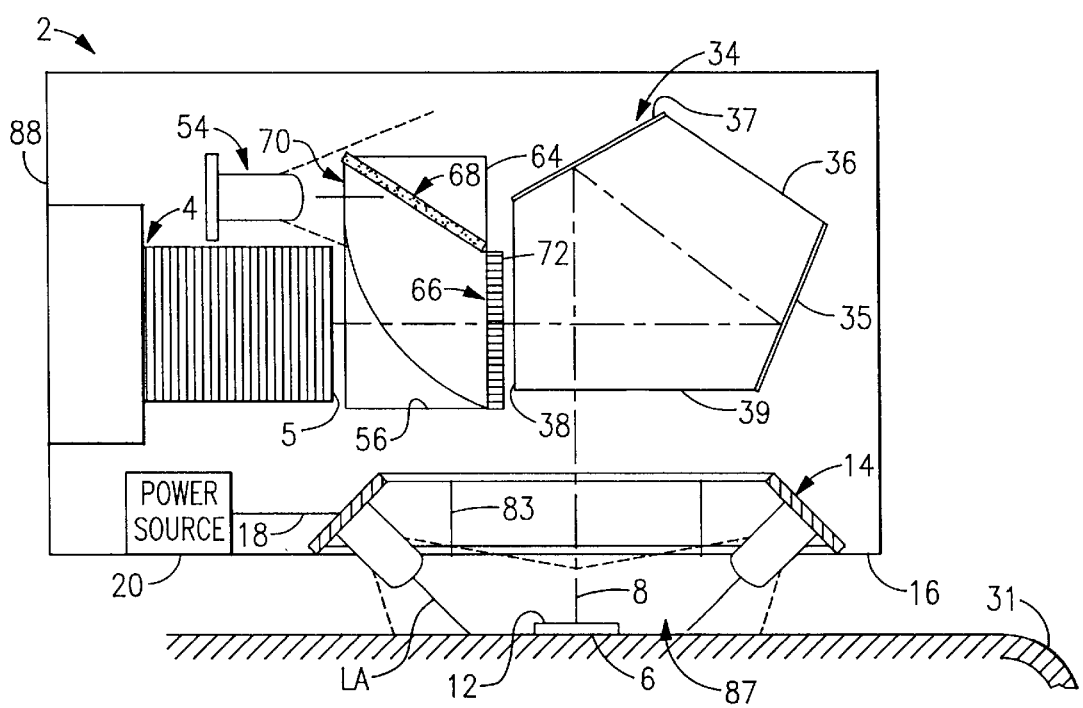
FIG. 8 is a diagrammatic representation of an eighth embodiment of the inspection system according to the present invention.

Turning now to FIG. 8, an eighth embodiment of the present invention will now be described. As this embodiment is very similar to the seventh embodiment, only the variations between this embodiment and the seventh embodiment will be described in detail. The primary difference between the eighth embodiment and the seventh embodiment is the elimination of the field lens 10 in this embodiment.

During use, the light from the LEDs 14 is supplied toward the object 6 to be inspected. In addition, light is also supplied along the optical axis 8 via the illumination source 50. The light supplied from the illumination source 50 is directed at the penta-prism 34 which, in turn, reflects the supplied light off the first and second reflective surfaces 35, 37 toward the object 6 for supplying illumination along the optical axis 8. Some of the light supplied by the two light sources 14, 50 is reflected by the surface 12 of the object 6 to be inspected to the surrounding environment. The remaining light, supplied by the two light sources 14, 50, is reflected off the surface 12 of the object 6 along the optical axis 8 toward the penta-prism 34. The light enters the second transmissive surface 39 of the penta-prism 34, which is arranged substantially normal to the optical axis 8, so the light passes substantially directly therethrough. The light then is reflected off the second reflective surface 37 of the penta-prism 34 toward the first reflective surface 35 of the penta-prism. The light then reflects off the first reflective surface 35 of the penta-prism and exits through the first transmissive surface 38 of the penta-prism toward the microlouver 72. Light passes through the microlouver 72 and is supplied toward then the curved beam splitter 58. The beam splitter 58 reflects a desired amount of light, e.g. between about 20% to 80% and preferably about 50%, back toward the diffuser 68 while-allowing a desired amount of reflected light, e.g. about 20% to 80% and preferably about 50%, reflected by the object 6 to be inspected to pass therethrough and enter the lens entrance aperture 5 of the camera 4. The focused light finally enters the camera 4 and is appropriately sensed by the internal sensing characteristics of the camera 4.

Figure 9:
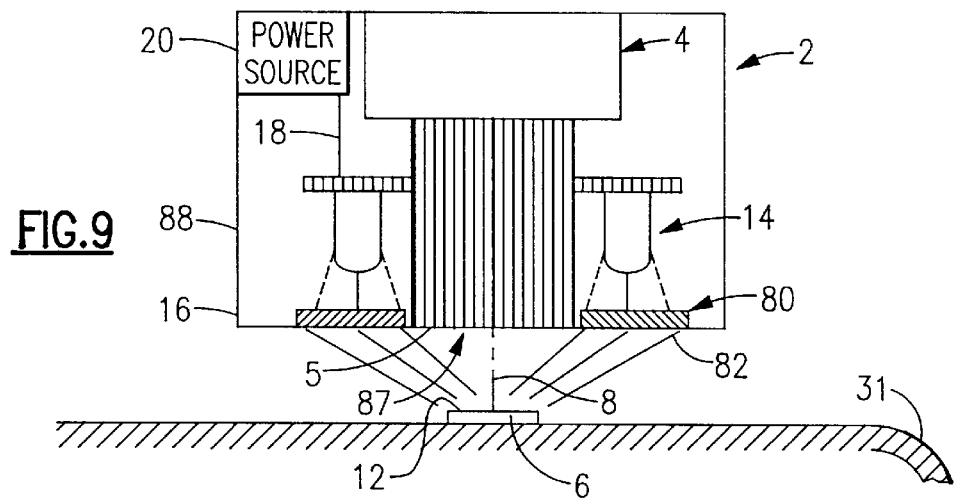
FIG. 9 is a diagrammatic representation of a ninth embodiment of the inspection system according to the present invention.

With reference to FIG. 9, a ninth embodiment of the present invention will now be described in detail. As this embodiment is very similar to the first embodiment, only the variations between this embodiment and the first embodiment will be described in detail. The primary difference between the ninth embodiment and the first embodiment is the addition of a Fresnel ring lens 80, which is positioned between the ring of LEDs 14 and the object 6 to be inspected. Preferably the Fresnel ring lens 80 is located closely adjacent the ring of LEDs 14 to prevent direct illumination of the object 6 by any of the LEDs 14.

During use, the light from the LEDs 14 is supplied to a rear surface of the Fresnel ring lens 80 and is emitted from a front surface 82 thereof toward the object 6 to be inspected. Some of the light supplied by the Fresnel ring lens 80 is reflected by the surface 12 of the object 6 to be inspected to the surrounding environment. The remaining light, supplied by the Fresnel ring lens 80, is reflected off the surface 12 of the object 6 along the optical axis 8 toward the lens entrance aperture 5 of the camera 4. The focused light enters the camera 4 and is appropriately sensed by the internal sensing characteristics of the camera 4.

Figure 10:
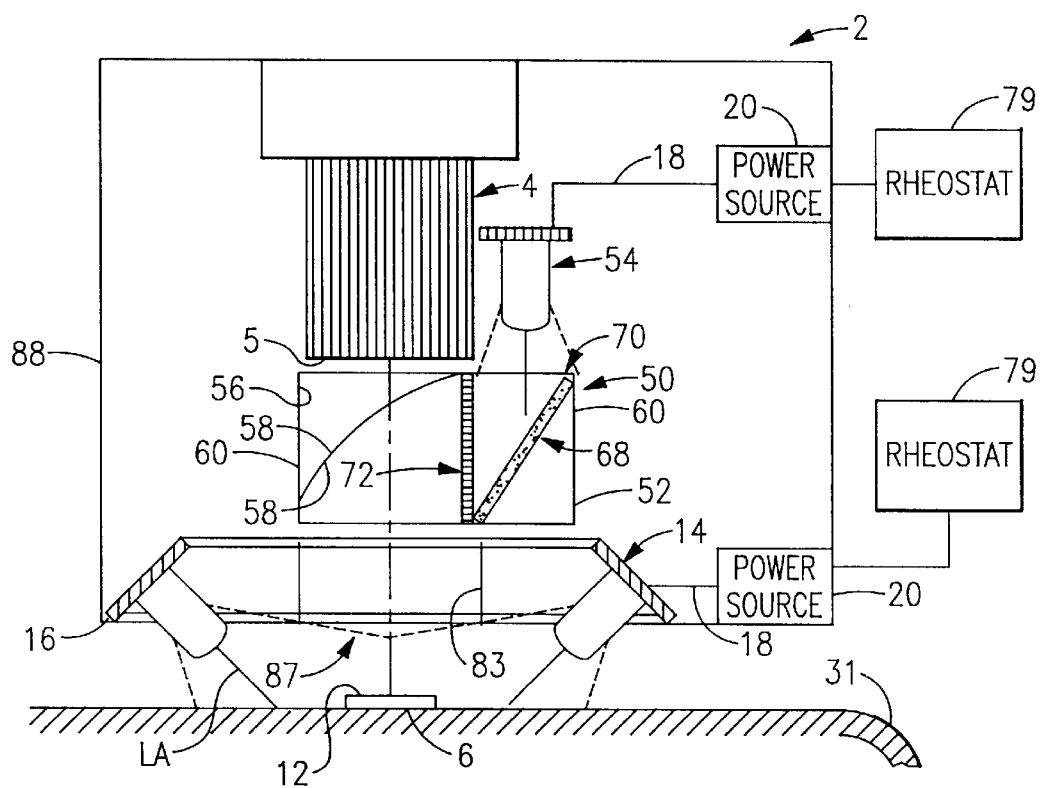
FIG. 10 is a diagrammatic representation of a tenth embodiment of the inspection system according to the present invention.

With reference to FIG. 10, a tenth embodiment of the present invention will now be described in detail. As this embodiment is very similar to the fifth embodiment, only the variations between this embodiment and the fifth embodiment will be described in detail. The primary difference between the tenth embodiment and the fifth embodiment is the elimination of the field lens 10 in this embodiment. In addition, the camera 4 is located somewhat closer to the object 6 to be inspected.

During use, the light from the LEDs 14 is supplied toward the object 6 to be inspected. In addition, light is also supplied along the optical axis 8 via the illumination source 50. Some of the light supplied by the two light sources 14, 50 is reflected by the surface 12 of the object 6 to be inspected to the surrounding environment. The remaining light, supplied by the two light sources 14, 50, is reflected off the surface 12 of the object 6 along the optical axis 8 toward the curved beam splitter 58. The beam splitter 58 reflects a desired amount of light, e.g. between about 20% to 80% and preferably about 50%, back toward the microlouver 72 while allowing a desired amount of reflected light, e.g. about 20% to 80% and preferably about 50%, reflected by the object 6 to be inspected to pass therethrough and enter the lens entrance aperture 5 of the camera 4. The focused light finally enters the camera 4 and is appropriately sensed by the internal sensing characteristics of the camera 4.

Figure 11:
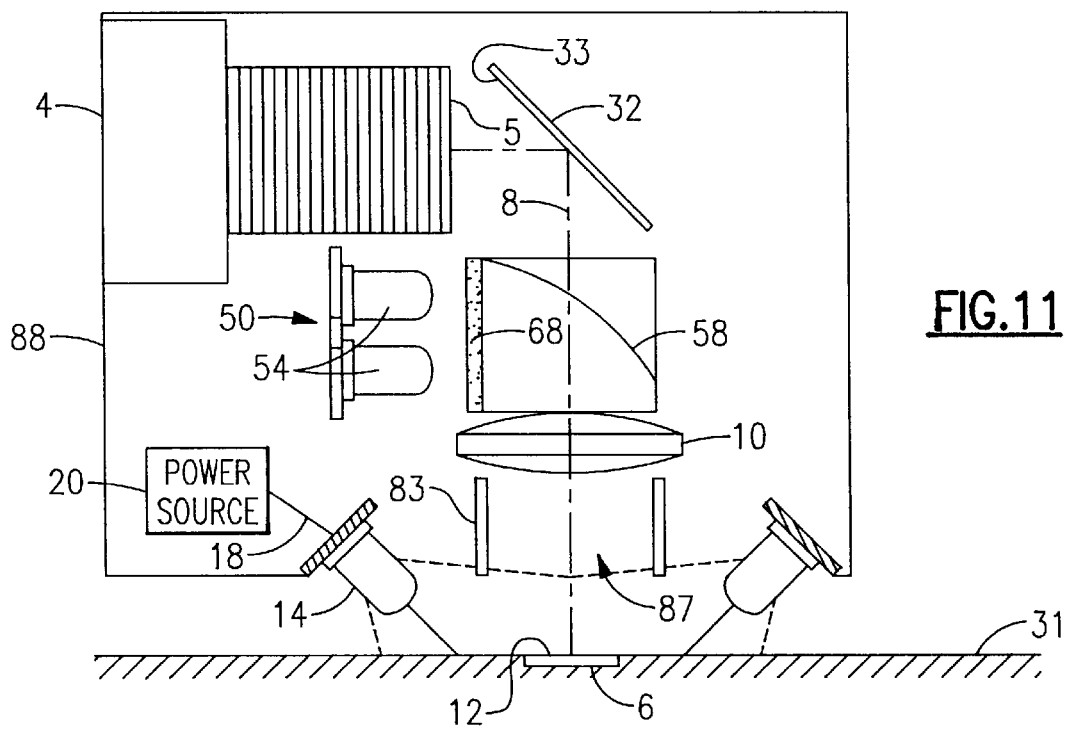
FIG. 11 is a diagrammatic representation of an eleventh embodiment of the inspection system according to the present invention.

With reference to FIG. 11, an eleventh embodiment of the present invention will now be described in detail. As this embodiment is very similar to the sixth embodiment, only the variations between this embodiment and the sixth embodiment will be described in detail. The primary difference between the eleventh embodiment and the sixth embodiment is the location of the diffuse illumination source 50 provided along the optical axis 8. According to this embodiment, the illumination source 50 is positioned, along the optical axis, at a location between the mirror 32 and the field lens 10, to provide illumination along the optical axis 8. Secondly, the illumination source 50 does not contain a microlouver and the arrangement of the illumination source 50 is sightly different from the embodiment of FIG. 5. In particular, the supplied light from the illumination source 54 illuminates a rear surface of the diffuser 68 while a front surface of the diffuser 68 emits the diffused light to the curved beam splitter 58. The beam splitter 58 reflects a desired amount of supplied light, e.g. between about 20% to 80% and preferably about 50%, along the optical axis 8 toward the object 6 while also allowing a desired amount of light, e.g. about 20% to 80% and preferably about 50%, of the light reflected by the surface 12 of the object 6 to pass through the beam splitter 58 and be viewed by the camera 4. In all other respect, this embodiment is similar to the sixth embodiment. This arrangement allows use of a small sized illumination source 50 but also increases slightly the height of the inspection system 2, e.g. by about ¾" or so.

Figure 12:
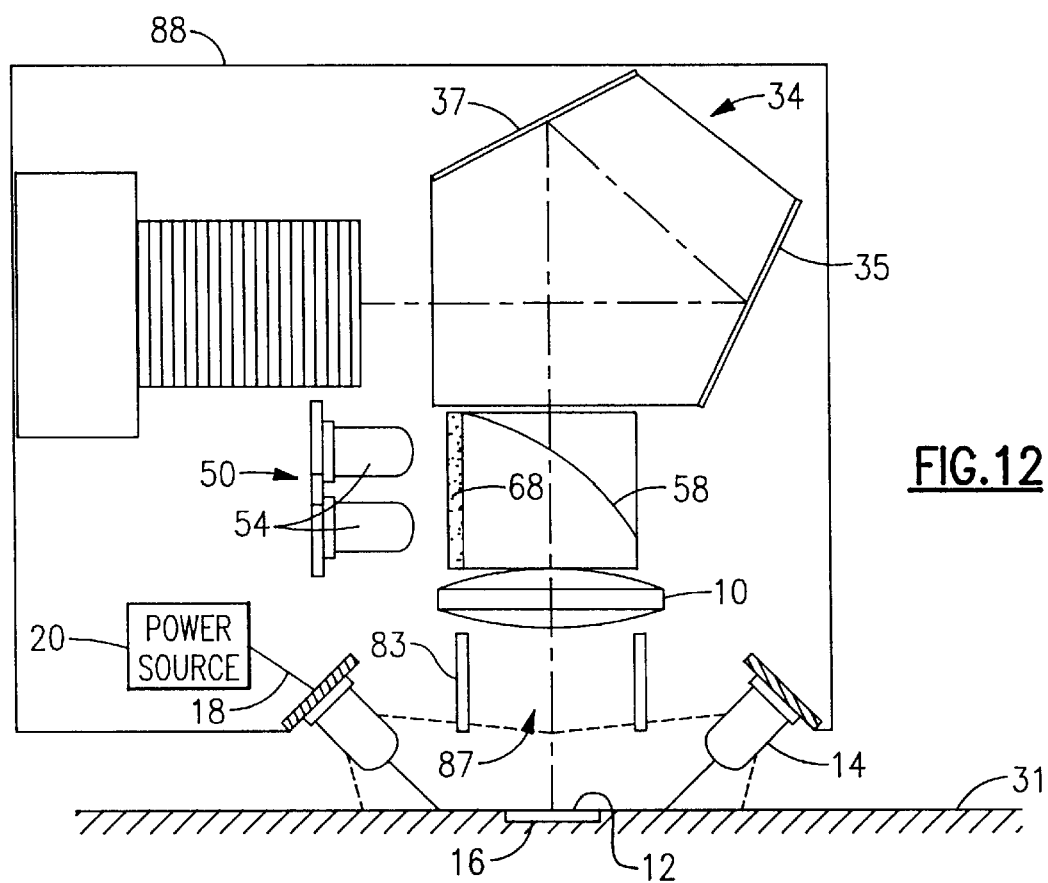
FIG. 12 is a diagrammatic representation of a twelfth embodiment of the inspection system according to the present invention.

Turning now to FIG. 12, a twelfth embodiment of the present invention will now be described in detail. As this embodiment is very similar to the seventh embodiment, only the variations between this embodiment and the seventh embodiment will be described in detail. The primary difference between the twelfth embodiment and the seventh embodiment is the location of the diffuse illumination source 50 provided along the optical axis 8. According to this embodiment, the illumination source 50 is positioned, along the optical axis, at a location between the penta-prism 34 and the field lens 10, to provide illumination along the optical axis 8. Secondly, the illumination source 50 is similar to the embodiment of FIG. 11. In all other respect, this embodiment is similar to the seventh embodiment. This arrangement allows use of a small sized illumination source 50 but also increases slightly the height of the inspection system, e.g. by about ¾" or so.

Figure 13:
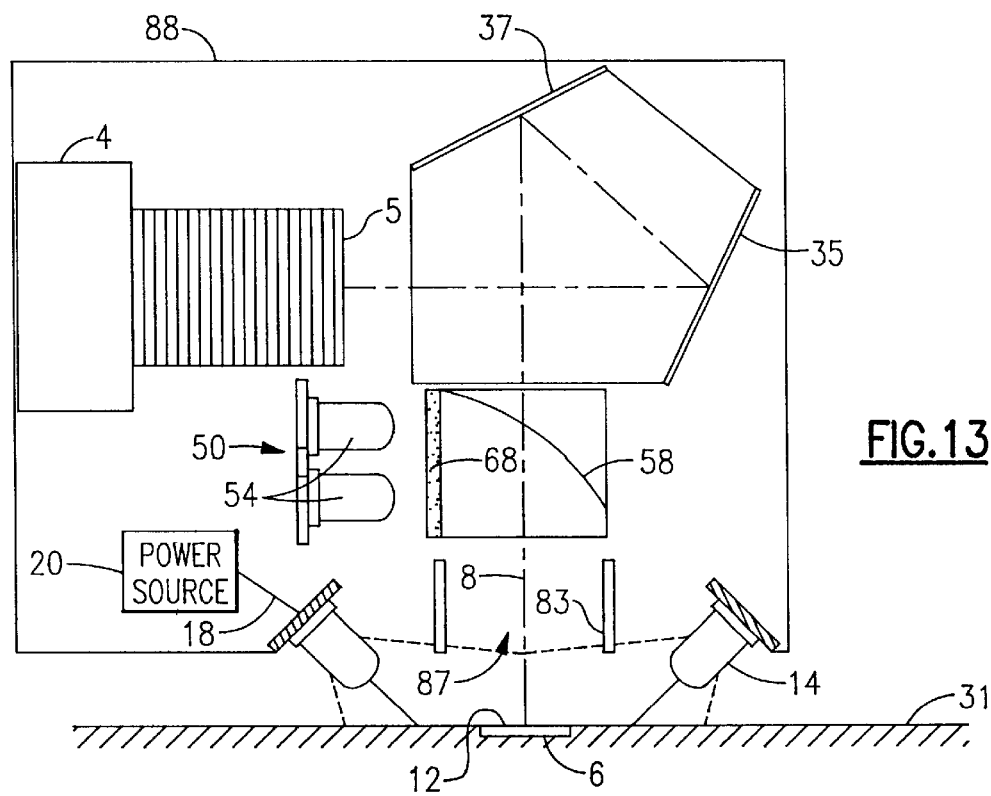
FIG. 13 is a diagrammatic representation of a thirteenth eighth embodiment of the inspection system according to the present invention.

With reference to FIG. 13, a thirteenth embodiment of the present invention will now be described in detail. As this embodiment is very similar to the eighth embodiment, only the variations between this embodiment and the eighth embodiment will be described in detail. The primary difference between the thirteenth embodiment and the eighth embodiment is the location of the diffuse illumination source 50 provided along the optical axis B. According to this embodiment, the illumination source 50 is positioned, along the optical axis, at a location between the penta-prism 34 and ring of LEDs 14, to provide illumination along the optical axis 8. Secondly, the illumination source 50, is similar to the embodiment of FIG. 11. In all other respects, this embodiment is similar to the eighth embodiment. This arrangement allows use of a small sized illumination source 50 but also increases slightly the height of the inspection system 2, e.g. by about ¾" or so.

Figure 14:
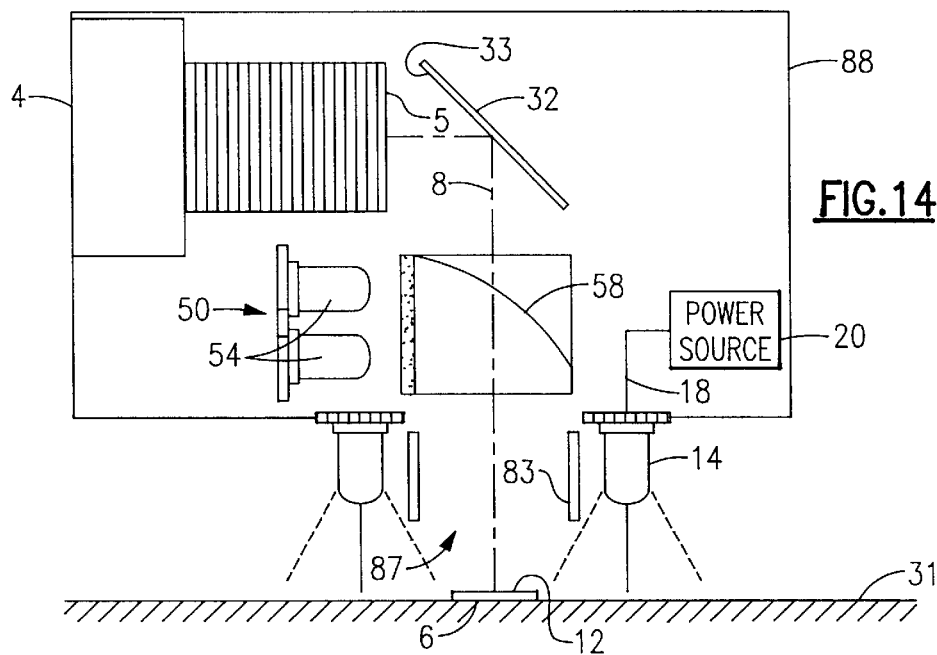
FIG. 14 is a diagrammatic representation of a fourteenth embodiment of the inspection system according to the present invention.

With reference to FIG. 14, a fourteenth embodiment of the present invention will now be described in detail. As this embodiment is very similar to the second embodiment, only the variations between this embodiment and the second embodiment will be described in detail. The primary difference between the fourteenth embodiment and the second embodiment is replacement of the field lens 10 with a diffuse illumination source 50. According to this embodiment, the illumination source 50 is positioned, along the optical axis, at a location between the mirror 32 and the ring of LEDs 14, to provide illumination along the optical axis 8. Secondly, the illumination source 50 is similar to the embodiment of FIG. 11. In all other respect, this embodiment is similar to the second embodiment. This arrangement allows use of a small sized illumination source 50 but also increases slightly the height of the inspection system 2, e.g. by about ¾" or so.

Figure 15:
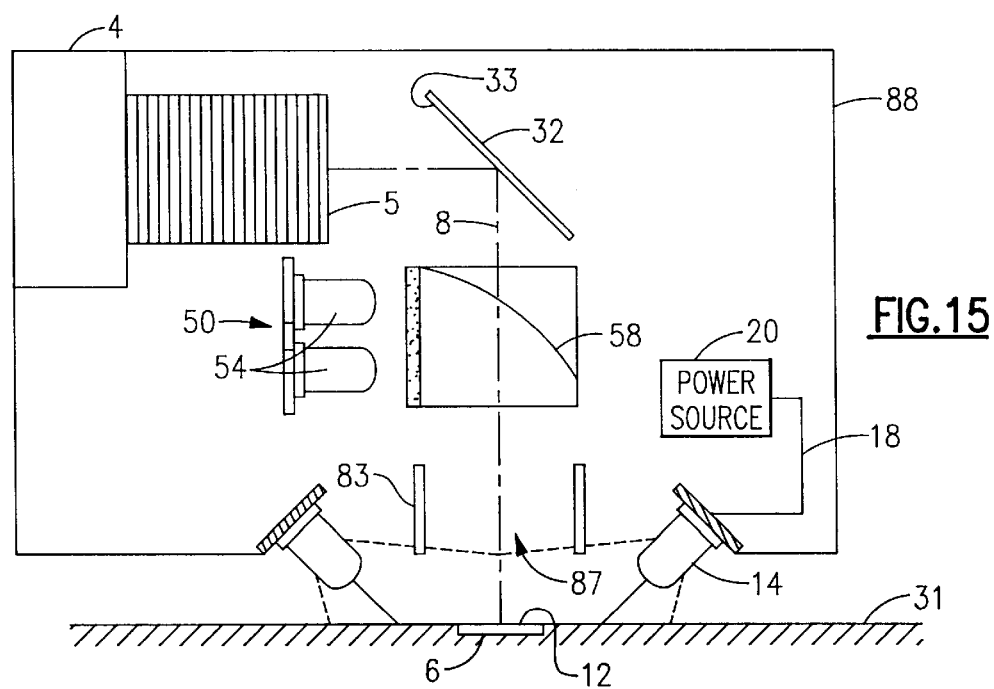
FIG. 15 is a diagrammatic representation of a fifteenth embodiment of the inspection system according to the present invention.

With reference to FIG. 15, a fifteenth embodiment of the present invention will now be described in detail. As this embodiment is very similar to the fourteenth embodiment, only the variations between this embodiment and the fourteenth embodiment will be described in detail. The primary difference between the fifteenth embodiment and the fourteenth embodiment is the use of a circuit which is bent into a conical or domed configuration in which all of the installed LEDs (lighting elements) face inwardly toward the object 6, as with the embodiment of FIG. 5, instead of a planar ring of LEDs 14, as with the fourteenth embodiment. In all other respect, this embodiment is similar to the fourteenth embodiment. This arrangement allows use of a small sized illumination source 50 but also increases slightly the height of the inspection system 2, e.g. by about ¾" or so.

Figure 16:
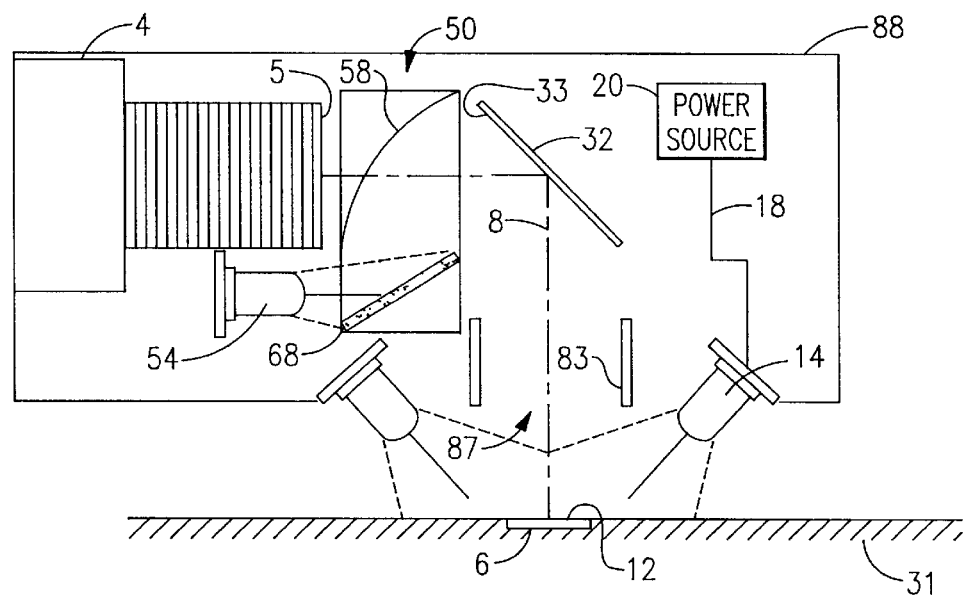
FIG. 16 is a diagrammatic representation of a sixteenth embodiment of the inspection system according to the present invention.

With reference to FIG. 16, a sixteenth embodiment of the present invention will now be described in detail. As this embodiment is very similar to the sixth embodiment, only the variations between this embodiment and the sixth embodiment will be described in detail. The primary difference between the sixteenth embodiment and the sixth embodiment is the elimination of the field lens 10 provided along the optical axis 8. In all other respect, this embodiment is similar to the sixth embodiment.

Figure 17:
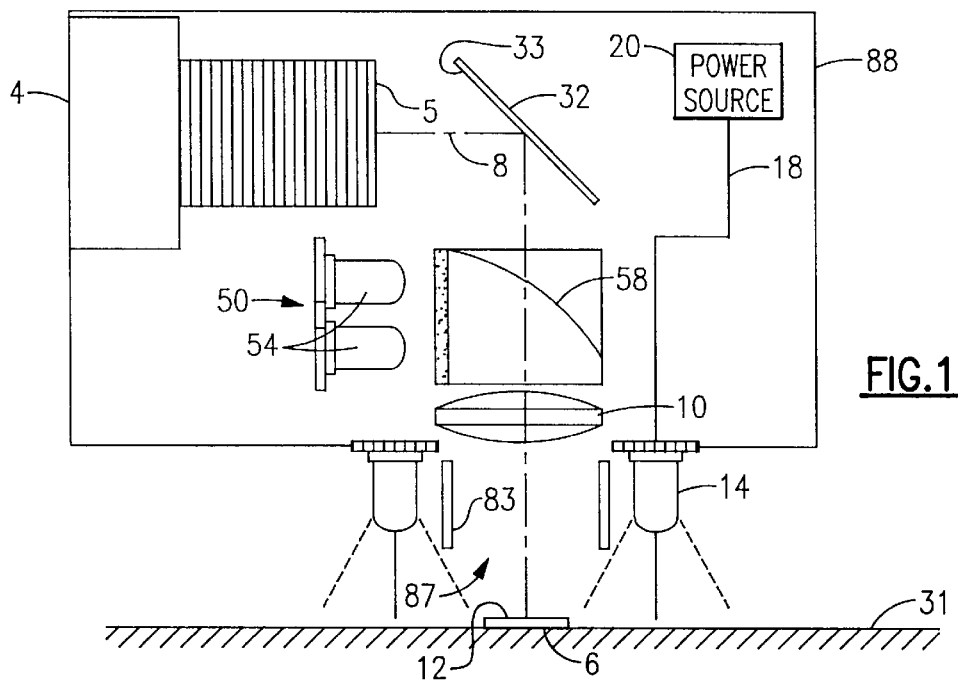
FIG. 17 is a diagrammatic representation of a seventeenth embodiment of the inspection system according to the present invention.

With reference to FIG. 17, a seventeenth embodiment of the present invention will now be described in detail. As this embodiment is very similar to the eleventh embodiment, only the variations between this embodiment and the eleventh embodiment will be described in detail. The primary difference between the seventeenth embodiment and the eleventh embodiment is the use of a planar ring of LEDs 14, as with the embodiment of FIG. 2, instead of a circuit which is bent into a conical or domed configuration with all of the installed LEDs (lighting elements) facing inwardly toward the object 6 as with the eleventh embodiment. In all other respect, this embodiment is similar to the sixth embodiment. This arrangement allows use of a small sized illumination source 50 but also increases slightly the height of the inspection system 2, e.g. by about ¾" or so.

Figure 18:
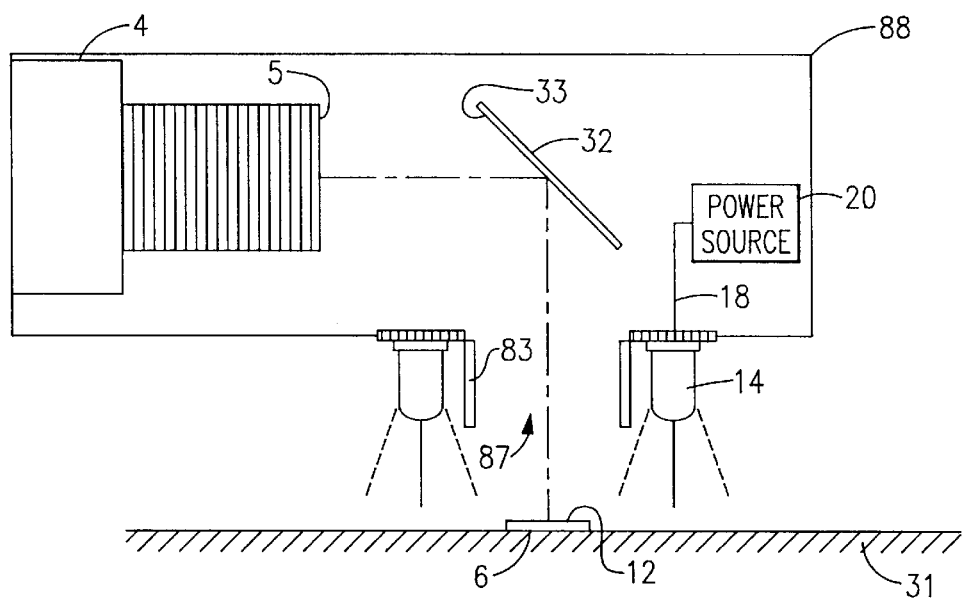
FIG. 18 is a diagrammatic representation of an eighteenth embodiment of the inspection system according to the present invention.

With reference to FIG. 18, an eighteenth embodiment of the present invention will now be described in detail. As this embodiment is very similar to the fourteenth embodiment, only the variations between this embodiment and the fourteenth embodiment will be described in detail. The primary difference between the eighteenth embodiment and the fourteenth embodiment is elimination of the diffuse illumination source 50, positioned along the optical axis, at a location between the mirror 32 and the ring of LEDs 14. In all other respect, this embodiment is similar to the second embodiment.

Figure 19:
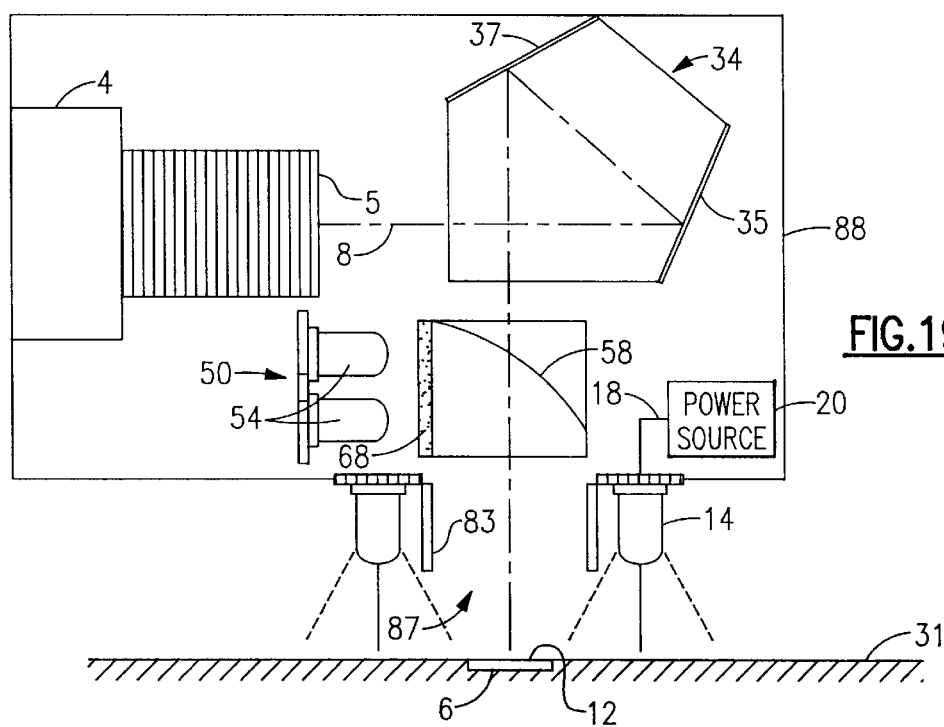
FIG. 19 is a diagrammatic representation of a nineteenth embodiment of the inspection system according to the present invention.

With reference to FIG. 19, a nineteenth embodiment of the present invention will now be described in detail. As this embodiment is very similar to the fourth embodiment, only the variations between this embodiment and the fourth embodiment will be described in detail. The primary difference between the nineteenth embodiment and the fourth embodiment is the addition of a diffuse illumination source 50 along the optical axis 8. According to this embodiment, the illumination source 50 is positioned, along the optical axis, at a location between the penta-prism 34 and ring of LEDs 14, to provide illumination along the optical axis 8. Secondly, a microlouver 72 in not required in this embodiment. Thirdly, the illumination source 50 is similar to the embodiment of FIG. 11. In all other respect, this embodiment is similar to the fourth embodiment. This arrangement allows use of a small sized illumination source 50 but also increases slightly the height of the inspection system 2, e.g. by about ¾" or so.

Figure 20:
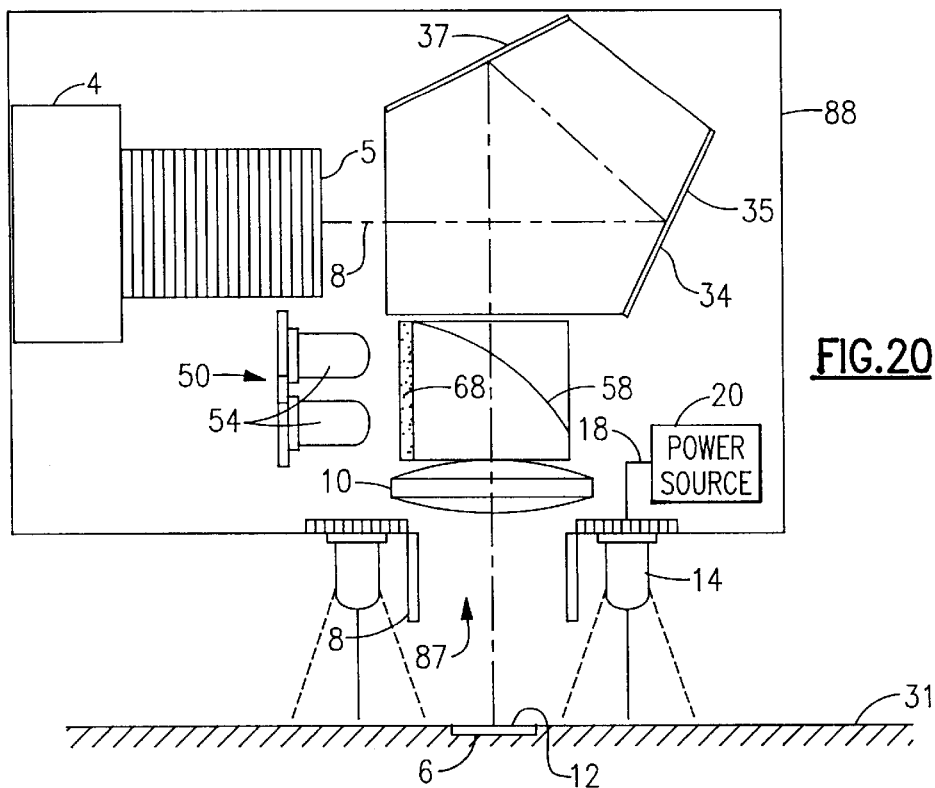
FIG. 20 is a diagrammatic representation of a twentieth embodiment of the inspection system according to the present invention.

With reference to FIG. 20, a twentieth embodiment of the present invention will now be described in detail. As this embodiment is very similar to the nineteenth embodiment, only the variations between this embodiment and the nineteenth embodiment will be described in detail. The primary difference between the twentieth embodiment and the nineteenth embodiment is the addition of a field lens 10 along the optical axis 8. According to this embodiment, the field lens 10 is positioned, along the optical axis, at a location between the illumination source 50 and the ring of LEDs 14, to provide illumination along the optical axis 8. In all other respect, this embodiment is similar to the nineteenth embodiment. This arrangement allows use of a small sized illumination source 50 but also increases slightly the height of the inspection system 2, e.g. by about ¾" or so.

Figure 21:
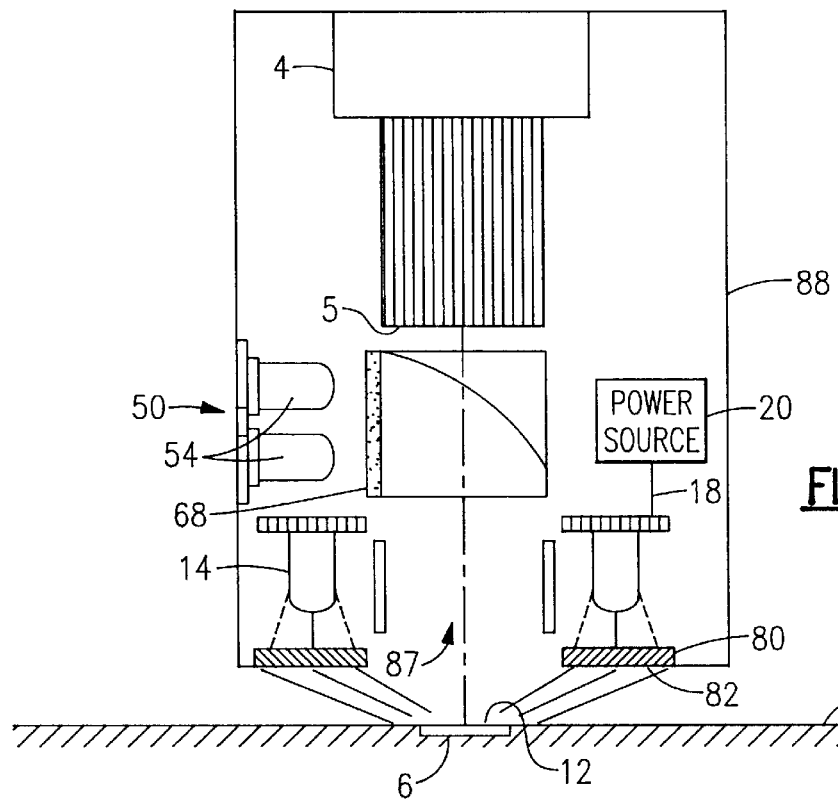
FIG. 21 is a diagrammatic representation of a twenty first embodiment of the inspection system according to the present invention.

With reference to FIG. 21, a twenty first embodiment of the present invention will now be described in detail. As this embodiment is very similar to the ninth embodiment, only the variations between this embodiment and the ninth embodiment will be described in detail. The primary difference between the twenty first embodiment and the ninth embodiment is that the camera 4 is spaced a further distance away from the object 6 and the addition of a diffuse illumination source 50 along the optical axis 8. According to this embodiment, the illumination source 50 is positioned, along the optical axis 8, at a location between the camera 4 and ring of LEDs 14, to provide illumination along the optical axis 8. In all other respect, this embodiment is similar to the ninth embodiment. This arrangement allows use of a small sized illumination source 50 but also increases slightly the height of the inspection system 2, e.g. by about ¾" or so.

Figure 22:
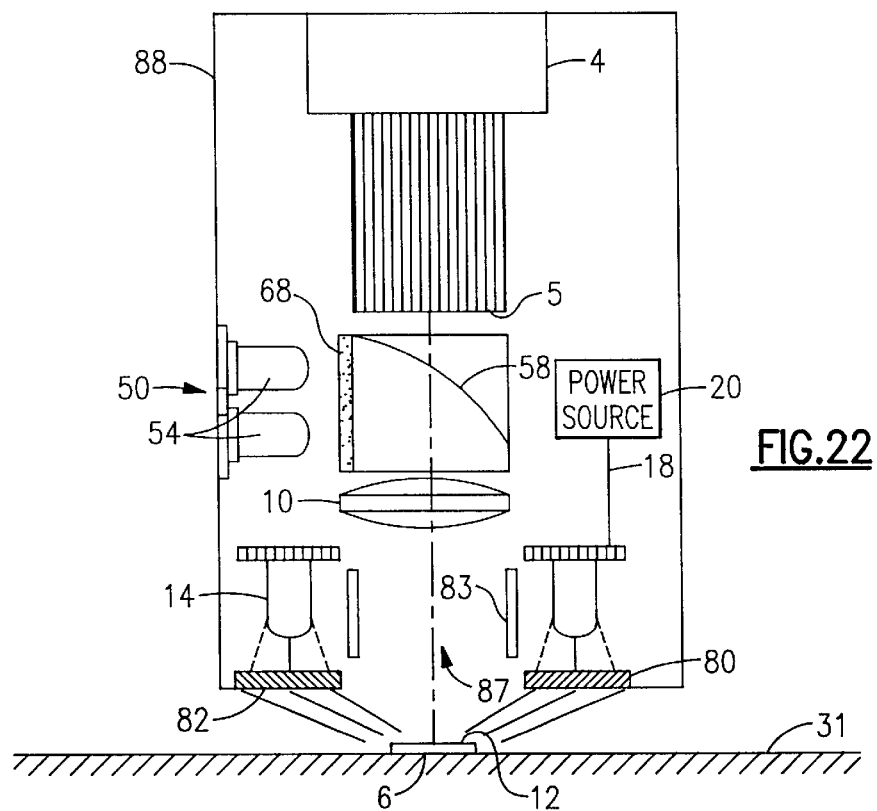
FIG. 22 is a diagrammatic representation of a twenty second embodiment of the inspection system according to the present invention.

With reference to FIG. 22, a twenty second embodiment of the present invention will now be described in detail. As this embodiment is very similar to the twenty first embodiment, only the variations between this embodiment and the twenty first embodiment will be described in detail. The primary difference between the twenty second embodiment and the twenty first embodiment is the addition of a field lens 10 along the optical axis 8. According to this embodiment, the field lens 10 is positioned, along the optical axis 8, at a location between the illumination source 50 and the ring of LEDs 14. In all other respect, this embodiment is similar to the ninth embodiment. This arrangement allows use of a small sized illumination source 50 but also increases slightly the height of the inspection system 2, e.g. by about ¾" or so.

Figure 23:
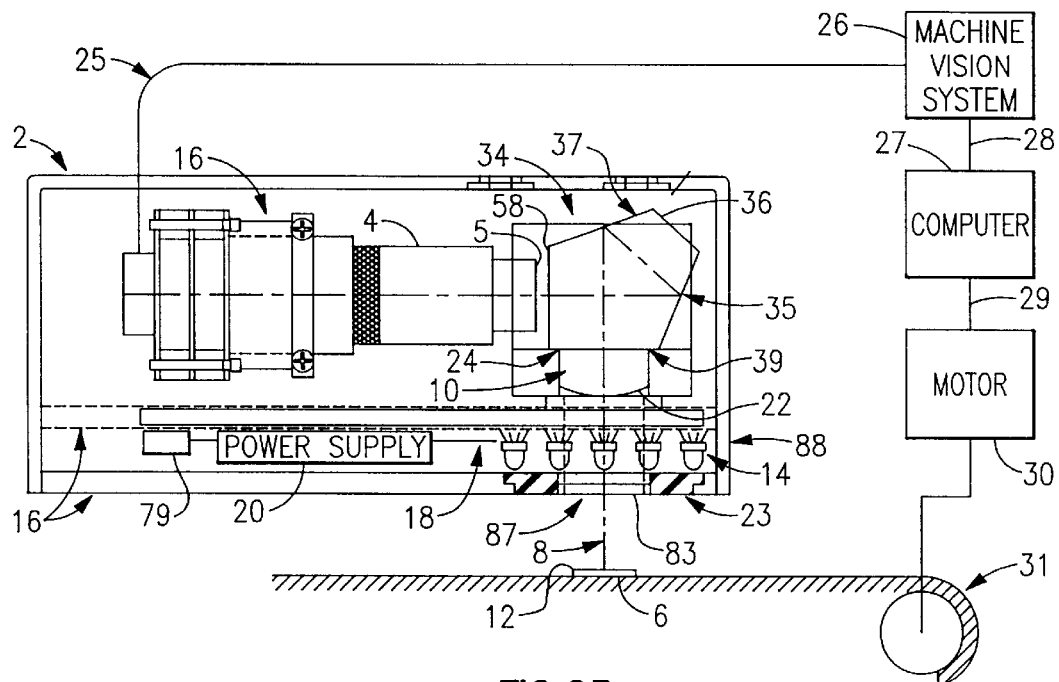
FIG. 23 is a diagrammatic representation of a twenty third embodiment of the inspection system according to the present invention.

Turning now to FIG. 23, a twenty third embodiment of the present invention will now be described. As can be seen is FIG. 23, the inspection system generally comprises a board-level miniature video camera 4, such as a CCD (charge coupled device) camera, a CMOS (metal oxide semiconductor) camera or some other observation or inspection device which is well known in the art. The camera 4 is positioned for viewing an object 6 to be inspected and an optical axis 8 is defined between the camera 4 and the object 6. A field lens 10 is positioned along the optical axis 8, at a location between a camera lens entrance aperture 5 and an inspection surface 12 of the object 6. It is to be appreciated that the field lens 10 is supported within the system 2 in a conventional manner (not shown in specific detail) such that the field lens 10 can be readily interchanged or replaced with a variety of other field lens, having different focusing characteristics, so that by selecting an appropriate power of the field lens a wide range of optical magnifications and/or fields of view can be achieved by the system 2.

Additionally, a penta-prism 34 is located along the optical axis 8 between the camera 4 and the field lens 10 to alter the path of the optical axis 8. The penta-prism 34 is supported conventionally within the system 2 in the same manner as the field lens 10. The penta-prism 34 has five surfaces 35, 36, 37, 38 and 39. Only two of these surfaces are utilized for reflecting light, e.g. the first and second reflective surfaces 35 and 37, respectively, while two other surfaces are utilized for transmitting light, e.g. the first and second transmissive surfaces 38 and 39, respectively.

A ring of LEDs 14 is affixed internally to the system 2, e.g. to the interior of a conventional framework 16 of the system, and the optical axis 8 extends through the center of the ring of LEDs 14. The ring of LEDs 14 is powered, via electrical wiring 18, by an appropriate power source 20 and the power is controlled by a rheostat 79 to facilitate desired illumination of the top surface of the object 6 to be inspected by the ring of LEDs 14 at different light intensities. A ring diffuser 23 is affixed to the underside of the conventional framework of the system and located between the ring of LEDs 14 and the top surface of the object 6 to be inspected such that the optical axis 8 additionally extends through the center of the ring diffuser 23.

During use, the light from the LEDs 14 is supplied through the diffuser 23 toward the object 6 to be inspected. Some of the light supplied by the ring of LEDs 14 through the diffuser 23 is reflected by the surface 12 of the object 6 to be inspected to the surrounding environment. The remaining light, supplied by the ring of LEDs 14, through the diffuser 23, is reflected off the surface 12 of the object 6 along the optical axis 8 toward the field lens 10. The reflected light enters a first surface 22 of the field lens 10 and is altered by the internal focusing characteristics of the field lens 10. The focused light exits the rear surface 24 of the field lens 10 and then is supplied to and enters the second transmissive surface 39 of the penta-prism 34, which is arranged substantially normal to the optical axis 8, so the light passes substantially directly therethrough and is substantially unaltered by the second transmissive surface 39.

The light then is reflected off the second reflective surface 37 of penta-prism 34 toward the first reflective surface 35 of the penta-prism 34. The light then reflects off the first reflective surface 35 of the penta-prism and exits through the first transmissive surface 38 of the penta-prism and is supplied toward the lens entrance aperture 5 of the camera 4. The focused light finally enters the camera 4, via the lens entrance aperture 5, and is appropriately sensed by the internal sensing mechanism of the camera 4.

The camera 4 is, in turn, coupled to a machine vision system 26 (only diagrammatically shown), via a conventional cable 25, for determining the sensed image, e.g. by a comparison of the sensed image with prior input features, images, characters, objects, contours, shapes, indicia, etc. Once the desired characteristic, feature, etc., of the object(s) 6 to be observed or inspected is determined by the system 2, the object(s) 6 can then be further manipulated by the system. The machine vision system 26, in turn, is connected to a computer 27 via a conventional cable 28. The computer 27 is typically electrically connected, by a cable 29, to a motor 30 which drives a conveyor 31 or some other transportation or conveying device for controlling further manipulation or manufacturing of the object 6. As the present invention primarily relates to the inspection system 2, a further detailed description concerning the machine vision system 26 and its associated components will not be provided.

Figure 24:
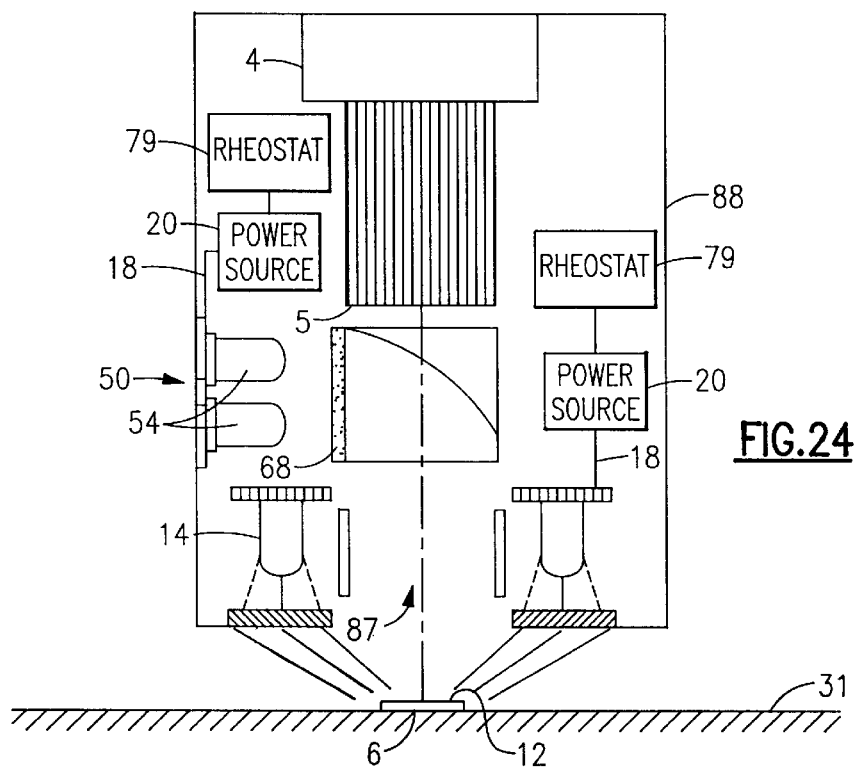
FIG. 24 is a diagrammatic representation of a twenty fourth embodiment of the inspection system according to the present invention.

With reference to FIG. 24, a twenty fourth embodiment of the present invention will now be described in detail. As this embodiment is very similar to the twenty first embodiment, only the variations between this embodiment and the twenty first embodiment will be described in detail. The major differences between the twenty fourth and the twenty first embodiments is the addition of a rheostat 79 to control power source 20 and facilitate control over the illumination character and intensity supplied by the ring of LEDs 14, and the addition of a second rheostat 79 to control the second power source 20 and thereby control the illumination character and intensity supplied by the diffused illumination source 50.

The light supplied by the ring of LEDs 14 is diffused by a frenel lens 80, or some other diffuser, to provide only diffuse off-axis illumination of the surface 12 of the object 6. In addition, the diffused illumination source 50 is positioned along the optical axis 8, at a location of between the camera lens entrance aperture 5 and the ring of LEDs 14, to provide diffuse illumination along the optical axis 8. If desired, the frenel lens 80 may be eliminated so that the ring of LEDs 14 supplies direct off-axis illumination of the surface 12 of the object 6.

By the disclosed arrangement, the two rheostats 79 allow both power sources 20 to be activated, at the same time, to provide illumination both along the optical axis 8 as well as supply light at an acute angle relative to the optical axis 8, i.e. supply light "off-axis". When both illumination sources 14, 50 are employed, the character and intensity of the two illumination sources can be matched to be substantially identical to one anther or one illumination source 14 or 50 can be controlled to have a different illumination intensity, e.g. be either brighter or darker, than the other illumination source 50 or 14. Alternatively, only one of the two illumination sources 14, 50 can be employed to supply light either along the optical axis 8, or at an acute angle relative thereto, and the rheostats 79 facilitate control of the character and intensity of the desired illumination source(s) 14 and/or 50.

It is to be appreciated that the penta-prism 34 is interchangeable with a pair of flat mirrors which may be disposed at angles of approximately 67.5° and 22.5° with respect to the optical axis 8 of the camera 4, or other combinations of angles which have the effect of redirecting the optical axis of the camera at approximately a right angle for viewing the surface 12 to be inspected. The purpose of the penta-prism or the pair of flat mirror surfaces is to twice invert the image of the object to be inspected so it is perceived by the camera 4 in a right side up fashion rather than in an inverted fashion.

It is to be appreciated that both light sources 14, 50 can be each coupled to a rheostat 79 (FIG. 10) or some other control device to facilitate control of the intensity and character of the light supplied by the ring of LEDs 14 and the illumination source 50 for providing light along the optical axis. This allows greater versatility to the system and ensures that the light provided by one of the two light sources will not dominate or hinder effective illumination of the object 6.

In all of the disclosed embodiments of the present invention, the system is preferably contained within a small exterior system housing 80. In the embodiments of FIGS. 1–4, 6–9, 16, 18 and 23, for example, the system housing 80 has a height dimension of no more than about 3¼ inches, and preferably a height of between 1.5 and 2.0 inches, a width dimension of about 1.5 inches, preferably a width dimension of between 1.25 and 1.75 inches, and a depth dimension of about 5 inches, and preferably a depth of between 4.5 and 5.5 inches. In the embodiments of FIGS. 5, 10–15, 17 and 19–22, for example, the system housing 80 has a height dimension of no more than about 2.5 inches, and preferably a height of between 1.5 and 2.0 inches, a width dimension of about 1.5 inches, preferably a width dimension of between 1.25 and 1.75 inches, and a depth dimension of about 4 inches, and preferably a depth of between 3.5 and 4.5 inches. The miniaturization or small size of the system housing 80, according to the present invention, facilitates placement of the system within the small confines of conventional semiconductor processing equipment.

The system housing 80 has at least one aperture 87 provided in a base surface thereof and all of the components which define or alter the optical axis 8 of the system 2 are arranged with in the system housing 80 so that the optical axis 8 extends through the at least one aperture 87 of the system housing. A ring light, or some other known or conventional illumination source, is affixed to the exterior of the system housing, adjacent the at least one aperture 87, and provided for supplying illumination at an angle with respect to the optical axis.

A cylindrical shield or ferrule 83, secured to and extending from the base of the framework 16, serves a number of functions. First, the ferrule 83 is preferably painted black on the inside to prevent "blow-back" of light from an LED of the ring of LEDs 14 back to the penta-prism and the camera lens, i.e. to absorb light supplied directly by any one of the LEDs. Second, the ferrule 83 is painted white on the outside to help disperse and diffuse light within the LED-ring circuit chamber of the ring of LEDs 14. Third, the ferrule 83 helps position the optical axis 8 properly with respect to the LED circuit. That is, the base of the housing 80 has at least one circular hole or aperture 87 provided therein and the ferrule 83 is the same size or slightly larger in size than the at least one aperture 87.

In a preferred form of the invention, the camera is a "board-level" camera which is particularly small in size. The small size of the camera is crucial to the utility and the function of the imaging module according to the present invention.

It is to be appreciated that a penta-prism 34 is preferred over a pair of mirror as any slight misalignment of the penta-prism, within a mounting slot, will still facilitate an accurate reflection of the light from the object at an angle of 90°. Secondly, the penta-prism is easy to clean because both transmissive surfaces are exposed (face outwardly) while, if two separate mirrors are employed, the reflective surfaces of the two separate mirrors face inwardly and are much more difficult to maintain in a clean condition. Lastly, the machining of the mounting member (s) for supporting the penta-prism is simpler than manufacturing a mounting arrangement for mounting two separate mirrors, e.g. cylindrical bores and right-angle cuts are required rather than narrow slots at odd angles.

In a preferred form of the invention, the penta-prism and the field lens are glued in place with optical UV-cured epoxy rather than by being fastened to the housing via mounting screws and/or retaining rings. Such attachment simplifies the machining of the apparatus and reduces the number of components thereby further minimizing the chances of damaging the optical components during assembly or at the inspection site.

Preferably, the field lens is an off-the-shelf 25 mm "lipstick" lens. It is to be appreciated, however, that the use of 50 mm achromat field lens also allow a desired field of view (4.5 mm×6.00 mm) to be achieved at the required distance dictated by the penta-prism and the light source dimensions. However, the inventors have determined that placing the field lens between the camera lens and the penta-prism, rather than placing the field lens between the penta-prism and the object, generally does not provide satisfactory optical results.

Since certain changes may be made in the above described observation system, without departing from the spirit and scope of the invention herein involved, it is intended that all of the subject matter of the above description or shown in the accompanying drawings shall be interpreted merely as examples illustrating the inventive concept herein and shall not be construed as limiting the invention.

What is claimed is:

1. A compact miniature inspection system for observing an object, the inspection system comprising:
    a housing having an observation aperture therein;
    a board level camera, located within the housing, for inspecting an object when located at an inspection location, and an optical axis being defined between an entrance aperture lens of the board level camera and the inspection location and extending through the aperture in the housing;
    a ring light, supported by the housing, for providing light to the object to be inspected, the ring light being located concentrically with respect to and along the optical axis, at a location between the lens of the camera and the inspection location; and a ferrule, supported by the housing, extending along the optical axis, the ferrule defining the observation aperture of the housing and, the ferrule being locate between the ring light and the optical axis to separate the ring light from the optical axis, and
    an inwardly facing surface of the ferrule being non-reflective with respect to any supplied light to function as a light trap and absorb any stray light.

2. The compact miniature inspection system according to claim 1, wherein a field lens is located along the optical axis at a location between the lens of the board level camera and the object, when placed at the object observing location.

3. The compact miniature inspection system according to claim 2, wherein the compact miniature inspection system further includes one or more of the following:
    a mirror being located along the optical axis, between the lens of the board level camera and the field lens, and light reflected by the object along the optical axis being reflected by the mirror toward the lens of the board level camera;
    a penta-prism being located along the optical axis, between the lens of the board level camera and the field lens, and light reflected from the object along the optical axis is reflected by the Pena-prism toward the lens of the board level camera;
    an illumination source, for providing illumination along the optical axis of the miniature inspection system, being provided at a location between the lens of the board level camera and the field lens, and the illumination source includes a beam splitter located along the optical axis for reflecting illumination from the illumination source along the optical axis and for allowing a portion of the light reflected by the object to be inspected to pass through the beam splitter and enter the lens of the board level camera; and
    a diffuser, supported by the housing, is located between the ring light and the inspection location to diffuse the light supplied by the ring light to the object when located at the inspection location.

4. The compact miniature inspection system according to claim 1, wherein a penta-prism is located along the optical axis, between the lens of the board level camera and the object when placed at the object observing location, and light reflected from the object along the optical axis being reflected by the penta-prism toward the lens of the board level camera.

5. The compact miniature inspection system according to claim 4, wherein the compact miniature inspection system further includes one or more of the following:
    a field lens being located along the optical axis at a location between the lens of the board level camera and the object, when placed at the object observing location; and
    an illumination source, for providing illumination along the optical axis of the miniature inspection system, being provided at a location between the lens of the board level camera and the object when placed at the object observing location, and the illumination from the illumination source along the optical axis and for allowing a portion of the light reflected by the object to be inspected to pass through the beam splitter and enter the lens of the board level camera.

6. The compact miniature inspection system according to claim 1, wherein an illumination source, for providing illumination along the optical axis of the miniature inspection system, being provided at a location between the lens of the board level camera and the object when placed at the object observing location, and the illumination source includes a beam splitter located along the optical axis for reflecting illumination from the illumination source along the optical axis and for allowing a portion of the light reflected by the object to be inspected to pass through the beam splitter and enter the lens of the board level camera.

7. The compact miniature inspection system according to claim 6, wherein the compact miniature inspection system further includes one or more of the following:
    a mirror being located along the optical axis, between the lens of the board level camera and the object when placed at the object observing location, and light reflected by the object along the optical axis being reflected by the mirror toward the lens of the board level camera;

a penta-prism being located along the optical axis, between the lens of the board level camera and the object when placed at the object observing location, and light reflected from the object along the optical axis being reflected by the Pena-prism toward the lens of the board level camera;

a field lens is located along the optical axis at a location between the lens of the board level camera and the object, when placed at the object observing location; and a diffuser, supported by the housing, is located between the ring light and the inspection location to diffuse the light supplied by the ring light to the object when located at the inspection location.

8. The compact miniature inspection system according to claim 1, wherein a mirror is located along the optical axis, between the lens of the board level camera and the object when placed at the object observing location, and light reflected by the object along the optical axis being reflected by the mirror toward the lens of the board level camera.

9. The compact miniature inspection system according to claim 6, wherein the compact miniature inspection system further includes one or more of the following:

an illumination source, for providing illumination along the optical axis of the miniature inspection system, being provided at a location between the lens of the board level camera and the object when placed at the object observing location, and the illumination source includes a beam splitter located along the optical axis for reflecting illumination from the illumination source along the optical axis and for allowing a portion of the light reflected by the object to be inspected to pass through the beam splitter and enter the lens of the board level camera;

a penta-prism being located along the optical axis, between the lens of the board level camera and the object when placed at the object observing location, and light reflected from the object along the optical axis being reflected by the Pena-prism toward the lens of the board level camera;

a field lens is located along the optical axis at a location between the lens of the board level camera and the object, when placed at the object observing location; and a diffuser, supported by the housing, is located between the ring light and the inspection location to diffuse the light supplied by the ring light to the object when located at the inspection location.

10. The compact miniature inspection system according to claim 1, wherein the compact miniature inspection system further includes one or more of the following:

a diffuser, supported by the housing, is located between the ring light and the object when placed at the object observing location, to diffuse the light supplied by the ring light to the object wen located at the inspection location;

the ring light is connected to a power source which controls ta least one of an intensity and a character of the illumination supplied by the ring light; and a fresnel lens is located adjacent the ring light, between the ring light and the object when located at the object observing location, for altering the light supplied to the object when placed at the object inspection location and preventing direct illumination of the object.

11. The compact miniature inspection system according to claim 1, wherein the ring light is conical in shape, tapering from a wider dimension to a narrower dimension, and supports a plurality of LEDs, and the plurality of LEDs of the ring light are aligned to provide direct illumination of the object to be inspected.

12. The compact miniature inspection system according to claim 3, wherein both the ring light and the illumination source, for providing illumination along the optical axis, are each powered by a power source and a mechanism is provided for controlling both the intensity and character of the light supplied by the ring light and the illumination source for providing illumination along the optical axis.

13. The compact miniature inspection system according to claim 5, wherein both the ring light and the illumination source, for providing illumination along the optical axis, are each powered by a power source and a mechanism is provided for controlling both the intensity and character of the light supplied by the ring light and the illumination source for providing illumination along the optical axis.

14. The compact miniature inspection system according to claim 6, wherein both the ring light and the illumination source, for providing illumination along the optical axis, are each powered by a power source and a mechanism is provided for controlling both the intensity and character of the light supplied by the ring light and the illumination source for providing illumination along the optical axis.

15. The compact miniature inspection system according to claim 9, wherein both the ring light and the illumination source, for providing illumination along the optical axis, are each powered by a power source and a mechanism is provided for controlling both the intensity and character of the light supplied by the ring light and the illumination source for providing illumination along the optical axis.

16. The miniature inspection system according to claim 1, in combination with a vision system which is electrically coupled to said compact miniature inspection system, a computing mechanism which is electrically coupled to said vision system, and a conveying mechanism which is electrically coupled to said computing mechanism, and said vision system supplies a sensed image of the object to be inspected to said computing mechanism which determines one of a characteristic and a feature of said object and outputs a signal to said conveying mechanism to control further manipulation of said object in view of one of the determined characteristic or feature.

17. A miniature inspection system for observing an object, the inspection system comprising:

a housing having an observation aperture therein;

a camera, located within the housing, for inspecting an object when located at an inspection location, and an optical axis being defined between a lens of the camera and the inspection location and extending through the aperture in the housing;

a surrounding light, supported by the housing, for providing light to the object to be inspected, the surrounding light being located concentrically with respect to and along the optical axis, at a location between an entrance aperture of the camera and the inspection location;

a field lens, located within the housing, being located along the optical axis, between the lens of the camera and the field lens;

at least one reflective surface, located within the housing, being located along the optical axis, between the lens of the camera and the field lens;

a ferrule, supported by the housing, extending along the optical axis, the ferrule defining the observation aperture of the housing and, the ferrule being located between the surrounding light and the optical axis to separate the surrounding light from the optical axis, and an inwardly facing surface of the ferrule being black to function as a light trap and absorb any stray light from the surrounding light; and a diffuser, supported by the housing, being located between the surrounding light and the inspection location to diffuse the light supplied by the surrounding light to the object when located at the inspection location.

18. The miniature inspection system according to claim 17, wherein the compact miniature inspection system further includes one or more of the following:

said at least one reflective surface is formed by a penta-prism;

the surrounding light is a planar surrounding light and contains a plurality of LEDs, and said plurality of LEDs are aligned with the diffuser to provide diffused illumination of the object to be inspected;

the surrounding light is powered by a power source which has a mechanism for controlling both an intensity and character of the light supplied by the surrounding light for providing illumination;

the camera is a board-level camera;

the field lens 50 mm is an achromat field lens; and the inspection system includes a system housing which has a height dimension of no greater than about 3¼ inches, a width dimension of about 1.5 inches, and a depth dimension of about 5 inches.

19. The miniature inspection system according to claim 17, in combination with a vision system which is electrically coupled to said miniature inspection system, a computing mechanism which is electrically coupled to said vision system, and a conveying mechanism which is electrically coupled to said vision system, and a conveying mechanism which is electrically coupled to said computing mechanism, and said vision system supplies a sensed image of the object to be inspected to said vision system supplies a sensed image of the object to be inspected to said computing mechanism which determines one of a characteristic and a feature of said object and outputs a signal to said conveying mechanism to control further manipulation of said object in view of one of said characteristic and feature.

* * * * *